US011753475B2

(12) United States Patent
Borges et al.

(10) Patent No.: US 11,753,475 B2
(45) Date of Patent: *Sep. 12, 2023

(54) BISPECIFIC-FC MOLECULES

(71) Applicant: AMGEN INC., Thousand Oaks, CA (US)

(72) Inventors: Luis G. Borges, Redwood City, CA (US); Patrick A. Baeuerle, Gauting (DE); Wei Yan, Sammamish, WA (US); Mark L. Michaels, Encino, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/885,998

(22) Filed: Feb. 1, 2018

(65) Prior Publication Data
US 2018/0230220 A1 Aug. 16, 2018

Related U.S. Application Data

(63) Continuation of application No. 14/210,178, filed on Mar. 13, 2014, now abandoned.

(60) Provisional application No. 61/791,424, filed on Mar. 15, 2013.

(51) Int. Cl.
| C07K 16/28 | (2006.01) |
| C07K 16/00 | (2006.01) |
| C07K 16/32 | (2006.01) |
| C07K 16/46 | (2006.01) |
| C07K 16/40 | (2006.01) |
| A61K 39/00 | (2006.01) |

(52) U.S. Cl.
CPC .......... *C07K 16/2863* (2013.01); *C07K 16/00* (2013.01); *C07K 16/28* (2013.01); *C07K 16/2803* (2013.01); *C07K 16/2809* (2013.01); *C07K 16/32* (2013.01); *C07K 16/40* (2013.01); *C07K 16/468* (2013.01); *A61K 2039/505* (2013.01); *C07K 2317/31* (2013.01); *C07K 2317/52* (2013.01); *C07K 2317/56* (2013.01); *C07K 2317/565* (2013.01); *C07K 2317/60* (2013.01); *C07K 2317/622* (2013.01); *C07K 2317/64* (2013.01); *C07K 2317/71* (2013.01); *C07K 2317/73* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| 5,637,481 A | 6/1997 | Ledbetter et al. |
| 6,737,056 B1 | 5/2004 | Presta |
| 7,083,784 B2 | 8/2006 | Dall'Acqua et al. |
| 7,670,600 B2 | 3/2010 | Dall'Acqua et al. |
| 7,695,936 B2 | 4/2010 | Carter et al. |
| 2003/0078385 A1 | 4/2003 | Arathoon et al. |
| 2003/0114659 A1 | 6/2003 | Winter et al. |
| 2007/0105199 A1 | 5/2007 | Yan et al. |
| 2009/0155275 A1 | 6/2009 | Wu et al. |
| 2009/0202532 A1* | 8/2009 | Kumagai ................ A61P 35/00 424/133.1 |
| 2009/0311253 A1 | 12/2009 | Ghayur et al. |
| 2010/0150918 A1* | 6/2010 | Kufer ................ C07K 16/3053 424/133.1 |
| 2010/0183615 A1 | 7/2010 | Kufer et al. |
| 2010/0234575 A1 | 9/2010 | Chamberlain et al. |
| 2012/0009181 A1 | 1/2012 | Ab et al. |
| 2012/0244578 A1 | 9/2012 | Kannan et al. |
| 2014/0302037 A1 | 10/2014 | Borges et al. |
| 2014/0302038 A1 | 10/2014 | Dimasi et al. |
| 2016/0145340 A1 | 5/2016 | Borges et al. |

FOREIGN PATENT DOCUMENTS

| WO | WO-2008/119567 A2 | 10/2008 | |
| WO | WO-2009/018386 A1 | 2/2009 | |
| WO | WO-2009/052081 A2 | 4/2009 | |
| WO | WO-2009/088805 A2 | 7/2009 | |
| WO | WO-2011/063348 A1 | 5/2011 | |
| WO | WO-2011063348 A1 * | 5/2011 | ............. C07K 16/00 |
| WO | WO-2012/125850 A1 | 9/2012 | |
| WO | WO-2012/135345 A1 | 10/2012 | |
| WO | WO-2012/135675 A2 | 10/2012 | |
| WO | WO-2012/143524 A2 | 10/2012 | |
| WO | WO-2013/026837 A1 | 2/2013 | |
| WO | WO-2013/055809 A1 | 4/2013 | |
| WO | WO-2013/096221 A1 | 6/2013 | |

OTHER PUBLICATIONS

Gunasekaran et al., J. Biol. Chem 285: 19637-19646 (Year: 2010).*
Chen et al., EMBO J. 14: 2784-2794 (Year: 1995).*
Wu et al., J Mol Biol 294: 151-162 (Year: 1999).*
Alt et al., Novel tetravalent and bispecific IgG-like antibody molecules combining single-chain diabodies with the immunoglobulin gamml Fc or CH3 region. *FEBS Lett.* 454(1-2): 90-4 (1999).
Bargou et al., Tumor regression in cancer patients by very low doses of a T cell-engaging antibody. *Science* 321 (5891): 974-7 (2008).
Chen et al., Enhancement and destruction of antibody function by somatic mutation: unequal occurrence is controlled by V gene combinatorial associations, *EMBO J.* 14(12):2784-94 (1995).
Desmyter et al., Antigen specificity and high affinity binding provided by one single loop of a camel single-domain antibody. *J. Biol. Chem.* 276(28): 26285-90 (2001).
Deyev et al., Multivalency: The hallmark of antibodies used for optimization of tumor targeting by design. *Bioessays* 30(9): 904-18 (2008).
Edelman et al., The covalent structure of an entire gammaG immunoglobulin molecule. *Proc. Natl. Acad. Sci. USA* 63(1): 78-85 (1969).

(Continued)

*Primary Examiner* — Phuong Huynh
(74) *Attorney, Agent, or Firm* — MARSHALL, GERSTEIN & BORUN LLP

(57) ABSTRACT

Described herein is a bispecific molecule containing an Fc polypeptide chain and immunoglobulin variable regions. Also provided are pharmaceutical formulations comprising such molecules, nucleic acids encoding such molecules, host cells containing such nucleic acids, methods of making such molecules, and methods of using such molecules.

8 Claims, 10 Drawing Sheets

Specification includes a Sequence Listing.

(56) References Cited

OTHER PUBLICATIONS

Fournier et al., Bispecific antibodies and trispecific immunocytokines for targeting the immune system against cancer: Preparing for the future. *Biodrugs* 27: 35-53 (2013).
Gunasekaran et al., Enhancing antibody Fc heterodimer formation through electrostatic steering effects: Applications to bispecific molecules and monovalent IgG. *J. Biol. Chem.* 285: 19637-46 (2010).
Honegger et al., Yet another numbering scheme for immunoglobulin variable domains: an automatic modeling and analysis tool. *J. Mol. Biol.* 309(3): 657-70 (2001).
Kipriyanov et al., Effect of Domain order on the activity of bacterially produced bispecific single-chain Fv antibodies. *J. Mol. Biol.* 330: 99-111 (2003).
Kussie et al., A Single engineered amino acid substitution changes antibody fine specificity, *J. Immunol.* 152(1):146-52 (1994).
Laible et al., Genetic engineering of goats for the production of a biosimilar antibody in milk. *Reprod. Fertil. Dev.* 25(1): 315 (2012).
Loffler et al., A recombinant bispecific single-chain antibody, CD19 x CD3, induces rapid and high lymphoma-directed cytotoxicity by unstimulated T lymphocytes. *Blood* 95(6): 2098-103 (2008).
Muyldermans et al., Single domain camel antibodies: current status. *J. Biotechnol.* 74(4): 277-302 (2001).
Park et al., Generation and characterization of a novel tetravalent bispecific antibody that binds to hepatitis B virus surface antigens. *Molec. Immunol.* 37(18): 1123-30 (2000).
Rudikoff et al., Single amino acid substitute altering antigen-binding specificity, *Proc. Natl. Acad. Sci. USA* 79:1979-83 (1982).
Scheller et al., Production of spider silk proteins in tobacco and potato. *Nature Biotechnol.* 19(6): 573-7 (2001).
Stancovski et al., Mechanistic aspects of the opposing effects of monoclonal antibodies to the ERBB2 receptor on tumor growth. *Proc. Natl. Acad. Sci. USA* 88: 8691-5 (1991).
Streltsov et al., Structure of a shark IgNAR antibody variable domain and modeling of an early-developmental isotype. *Protein Sci.* 14(11): 2901-9 (2005).
Xu et al., In vitro characterization of five humanized OKT3 effector function variant antibodies. *Cell Immunol.* 200(1): 16-26 (2000).
Ying et al., Soluble monomeric IgG1 Fc. *J. Biol. Chem.* 287(23): 19399-408 (2012).
Zhu et al., Production of human monoclonal antibody in eggs of chimeric chickens. *Nat. Biotechnol.* 23(9): 1159-69 (2005).

\* cited by examiner

SEQUENCE LISTING

<160> NUMBER OF SEQ ID NOS: 44

<210> SEQ ID NO 1
<211> LENGTH: 9

```
<212> TYPE: PRT
<213> ORGANISM: Artificial Sequence
<220> FEATURE:
<223> OTHER INFORMATION: Description of Artificial Sequence: Synthetic
      Amino acid sequence immediately preceding HC CDR1
<220> FEATURE:
<221> NAME/KEY: MOD_RES
<222> LOCATION: (2)..(9)
<223> OTHER INFORMATION: Any amino acid

<400> SEQUENCE: 1

Cys Xaa Xaa Xaa Xaa Xaa Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      Amino acid sequence preceding HC CDR2

<400> SEQUENCE: 2

Leu Glu Trp Ile Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      Amino acid sequence following HC CDR3
<220> FEATURE:
<221> NAME/KEY: MOD_RES
<222> LOCATION: (3)..(3)
<223> OTHER INFORMATION: Any amino acid

<400> SEQUENCE: 3

Trp Gly Xaa Gly
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      Amino acid sequence following LC CDR3
<220> FEATURE:
<221> NAME/KEY: MOD_RES
<222> LOCATION: (3)..(3)
<223> OTHER INFORMATION: Any amino acid

<400> SEQUENCE: 4

Phe Gly Xaa Gly
1

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      Amino acid sequence of anti-HER2 VH region

<400> SEQUENCE: 5

Glu Val Gln Leu Leu Glu Gln Ser Gly Ala Glu Leu Val Arg Pro Gly
1               5                   10                  15
```

```
Ala Leu Val Lys Leu Ser Cys Lys Ala Ser Gly Phe Lys Ile Lys Asp
            20                  25                  30

Tyr Phe Val Asn Trp Val Lys Gln Arg Pro Glu Gln Gly Leu Glu Trp
        35                  40                  45

Ile Gly Trp Ile Asp Pro Glu Asn Asp Asn Ser Leu Tyr Gly Pro Asn
    50                  55                  60

Phe Gln Asp Lys Ala Ser Ile Thr Ala Asp Thr Ser Ser Asn Thr Gly
65                  70                  75                  80

Tyr Leu Gln Leu Ser Gly Leu Thr Ser Glu Asp Thr Ala Val Tyr Tyr
                85                  90                  95

Cys Ala Leu Tyr Tyr Gly Ser Arg Gly Asp Ala Met Asp Tyr Trp Gly
            100                 105                 110

Gln Gly Thr Thr Val Thr Val
            115

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      Amino acid sequence of anti-HER2 VL region

<400> SEQUENCE: 6

Glu Leu Val Met Thr Gln Thr Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Ile Lys
            100                 105

<210> SEQ ID NO 7
<211> LENGTH: 125
<212> TYPE: PRT
<213> ORGANISM: Artificial Sequence
<220> FEATURE:
<223> OTHER INFORMATION: Description of Artificial Sequence: Synthetic
      Amino acid sequence of anti-CD3 VH region

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80
```

```
Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser
        115                 120                 125

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      Amino acid sequence of anti-CD3 VL region

<400> SEQUENCE: 8

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 9
<211> LENGTH: 518
<212> TYPE: PRT
<213> ORGANISM: Artificial Sequence
<220> FEATURE:
<223> OTHER INFORMATION: Description of Artificial Sequence: Synthetic
      Amino acid sequence of a single chain anti-HER2/CD3
      (P136629.3)P136629.3 aHer2(D3)scFv-aCD3(F12Q)scFv

<400> SEQUENCE: 9

Glu Val Gln Leu Leu Glu Gln Ser Gly Ala Glu Leu Val Arg Pro Gly
1               5                   10                  15

Ala Leu Val Lys Leu Ser Cys Lys Ala Ser Gly Phe Lys Ile Lys Asp
            20                  25                  30

Tyr Phe Val Asn Trp Val Lys Gln Arg Pro Glu Gln Gly Leu Glu Trp
        35                  40                  45

Ile Gly Trp Ile Asp Pro Glu Asn Asp Asn Ser Leu Tyr Gly Pro Asn
    50                  55                  60

Phe Gln Asp Lys Ala Ser Ile Thr Ala Asp Thr Ser Ser Asn Thr Gly
65                  70                  75                  80

Tyr Leu Gln Leu Ser Gly Leu Thr Ser Glu Asp Thr Ala Val Tyr Tyr
                85                  90                  95

Cys Ala Leu Tyr Tyr Gly Ser Arg Gly Asp Ala Met Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Gly Ser Glu Leu Val Met Thr Gln Thr Pro
    130                 135                 140
```

Ser Ser Leu Ser Ala Ser Leu Gly Asp Arg Val Thr Ile Ser Cys Arg
145                 150                 155                 160

Ala Ser Gln Asp Ile Ser Asn Tyr Leu Asn Trp Tyr Gln Gln Lys Pro
            165                 170                 175

Asp Gly Thr Val Lys Leu Leu Ile Tyr Tyr Thr Ser Arg Leu His Ser
        180                 185                 190

Gly Val Pro Ser Arg Phe Ser Gly Ser Gly Ser Gly Thr Asp Tyr Ser
    195                 200                 205

Leu Thr Ile Ser Asn Leu Glu Gln Glu Asp Ile Ala Thr Tyr Phe Cys
210                 215                 220

Gln Gln Gly Asn Thr Leu Pro Leu Thr Phe Gly Ala Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Ser Tyr Ala Met Asn Trp Val Arg Gln
    275                 280                 285

Ala Pro Gly Lys Gly Leu Glu Trp Val Ala Arg Ile Arg Ser Lys Tyr
290                 295                 300

Asn Asn Tyr Ala Thr Tyr Tyr Ala Asp Ser Val Lys Gly Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Val Ser Trp Trp Ala Tyr Trp Gly Gln Gly Thr
    355                 360                 365

Leu Val Thr Val Ser Ser Gly Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
    435                 440                 445

Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Ala Ala Ala Asp Tyr Lys Asp Asp Asp Asp Lys Gly Ser Ser
        500                 505                 510

His His His His His His
        515

<210> SEQ ID NO 10
<211> LENGTH: 742
<212> TYPE: PRT
<213> ORGANISM: Artificial Sequence
<220> FEATURE:

<223> OTHER INFORMATION: Description of Artificial Sequence: Synthetic
Amino acid sequence of an anti-HER2/CD3 Bi-Fc (P136632.3) D356K,
D399K, L234A, L235A P136632.3 (aHer2(D3)scFv-aCD3(F12Q)scFv-
FcAAKK)

<400> SEQUENCE: 10

```
Glu Val Gln Leu Leu Glu Gln Ser Gly Ala Glu Leu Val Arg Pro Gly
1               5                  10                  15

Ala Leu Val Lys Leu Ser Cys Lys Ala Ser Gly Phe Lys Ile Lys Asp
            20                  25                  30

Tyr Phe Val Asn Trp Val Lys Gln Arg Pro Glu Gln Gly Leu Glu Trp
        35                  40                  45

Ile Gly Trp Ile Asp Pro Glu Asn Asp Asn Ser Leu Tyr Gly Pro Asn
    50                  55                  60

Phe Gln Asp Lys Ala Ser Ile Thr Ala Asp Thr Ser Ser Asn Thr Gly
65                  70                  75                  80

Tyr Leu Gln Leu Ser Gly Leu Thr Ser Glu Asp Thr Ala Val Tyr Tyr
                85                  90                  95

Cys Ala Leu Tyr Tyr Gly Ser Arg Gly Asp Ala Met Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Gly Ser Glu Leu Val Met Thr Gln Thr Pro
    130                 135                 140

Ser Ser Leu Ser Ala Ser Leu Gly Asp Arg Val Thr Ile Ser Cys Arg
145                 150                 155                 160

Ala Ser Gln Asp Ile Ser Asn Tyr Leu Asn Trp Tyr Gln Gln Lys Pro
                165                 170                 175

Asp Gly Thr Val Lys Leu Leu Ile Tyr Tyr Thr Ser Arg Leu His Ser
            180                 185                 190

Gly Val Pro Ser Arg Phe Ser Gly Ser Gly Ser Gly Thr Asp Tyr Ser
        195                 200                 205

Leu Thr Ile Ser Asn Leu Glu Gln Glu Asp Ile Ala Thr Tyr Phe Cys
    210                 215                 220

Gln Gln Gly Asn Thr Leu Pro Leu Thr Phe Gly Ala Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Ser Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Gly Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Val Ser Trp Trp Ala Tyr Trp Gly Gln Gly Thr
        355                 360                 365

Leu Val Thr Val Ser Ser Gly Gly Gly Ser Gly Gly Gly Ser
    370                 375                 380
```

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
    435                 440                 445

Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Ala Ala Ala Glu Pro Lys Ser Ser Asp Lys Thr His Thr Cys
        500                 505                 510

Pro Pro Cys Pro Ala Pro Glu Ala Ala Gly Gly Pro Ser Val Phe Leu
    515                 520                 525

Phe Pro Pro Lys Pro Lys Asp Thr Leu Met Ile Ser Arg Thr Pro Glu
530                 535                 540

Val Thr Cys Val Val Val Asp Val Ser His Glu Asp Pro Glu Val Lys
545                 550                 555                 560

Phe Asn Trp Tyr Val Asp Gly Val Glu Val His Asn Ala Lys Thr Lys
            565                 570                 575

Pro Arg Glu Glu Gln Tyr Asn Ser Thr Tyr Arg Val Val Ser Val Leu
        580                 585                 590

Thr Val Leu His Gln Asp Trp Leu Asn Gly Lys Glu Tyr Lys Cys Lys
    595                 600                 605

Val Ser Asn Lys Ala Leu Pro Ala Pro Ile Glu Lys Thr Ile Ser Lys
610                 615                 620

Ala Lys Gly Gln Pro Arg Glu Pro Gln Val Tyr Thr Leu Pro Pro Ser
625                 630                 635                 640

Arg Lys Glu Met Thr Lys Asn Gln Val Ser Leu Thr Cys Leu Val Lys
            645                 650                 655

Gly Phe Tyr Pro Ser Asp Ile Ala Val Glu Trp Glu Ser Asn Gly Gln
        660                 665                 670

Pro Glu Asn Asn Tyr Lys Thr Thr Pro Pro Val Leu Lys Ser Asp Gly
    675                 680                 685

Ser Phe Phe Leu Tyr Ser Lys Leu Thr Val Asp Lys Ser Arg Trp Gln
690                 695                 700

Gln Gly Asn Val Phe Ser Cys Ser Val Met His Glu Ala Leu His Asn
705                 710                 715                 720

His Tyr Thr Gln Lys Ser Leu Ser Leu Ser Pro Gly Lys Ala Ala Ala
            725                 730                 735

His His His His His His
            740

<210> SEQ ID NO 11
<211> LENGTH: 2226
<212> TYPE: DNA
<213> ORGANISM: Artificial Sequence
<220> FEATURE:
<223> OTHER INFORMATION: Description of Artificial Sequence: Synthetic
      Nucleic acid sequence encoding SEQ ID NO:10 aHer2(D3)scFv-
      aCD3(F12Q)scFv-FcAAKK)

<400> SEQUENCE: 11

```
gaggtgcagc tgctcgagca gtctggagct gagcttgtga ggccaggggc cttagtcaag      60
ttgtcctgca aagcttctgg cttcaaaatt aaagactact ttgtgaactg ggtgaagcag     120
aggcctgaac agggcctgga gtggattgga tggattgatc ctgagaatga ataatagttta   180
tatgcccga acttccagga caaggccagt atcacagcag acacatcctc caacacaggc     240
tacctgcagc tcagcggcct gacatctgag gacactgccg tctattactg tgctctttat    300
tacggaagta gggggatgc tatggactac tggggccaag gaccacggt caccgtctcc      360
tcaggtggtg gtggttctgg cggcggcggc tccggtggtg gtggttctga gctcgtgatg    420
acccagactc catcctccct gtctgcctct ctgggagaca gagtcaccat cagttgcagg    480
gcaagtcagg acattagcaa ttatttaaac tggtatcagc agaaaccaga tggaactgtt    540
aaactcctga tctactacac atcaagatta cactcaggag tcccatcaag gttcagtggc    600
agtgggtctg gaacagatta ttctctcacc attagcaacc tggagcaaga agatattgcc   660
acttactttt gccaacaggg taatacgctt ccgctcacgt tcggtgctgg gaccaagctt    720
gagatcaaat ccggaggtgg tggatccgag gtgcagctgg tcgagtctgg aggaggattg    780
gtgcagcctg gagggtcatt gaaactctca tgtgcagcct ctggattcac cttcaatagc    840
tacgccatga actgggtccg ccaggctcca ggaaagggtt tggaatgggt tgctcgcata    900
agaagtaaat ataataatta tgcaacatat atgccgatt cagtgaaagg caggttcacc     960
atctccagag atgattcaaa aaacactgcc tatctacaaa tgaacaactt gaaaactgag    1020
gacactgccg tgtactactg tgtgagacat gggaacttcg gtaatagcta cgtttcctgg    1080
tgggcttact ggggccaagg gactctggtc accgtctcct caggtggtgg tggttctggc   1140
ggcggcggct ccggtggtgg tggttctcag actgttgtga ctcaggaacc ttcactcacc   1200
gtatcacctg gtgaacagt cacactcact tgtggctcct cgactggggc tgttacatct    1260
ggcaactacc caaactgggt ccaacaaaaa ccaggtcagg caccccgtgg tctaataggt   1320
gggactaagt tcctcgcccc cggtactcct gccagattct caggctccct gcttggaggc   1380
aaggctgccc tcaccctctc aggggtacag ccagaggatg aggcagaata ttactgtgtt   1440
ctatggtaca gcaaccgctg ggtgttcggt ggaggaacca aactgactgt cctagcggcc   1500
gcagagccca atcttctga caaaactcac acatgccccc gtgcccagc acctgaagca     1560
gctgggggac cgtcagtctt cctcttcccc ccaaaaccca aggacaccct catgatctcc   1620
cggacccctg aggtcacatg cgtggtggtg gacgtgagcc acgaagaccc tgaggtcaag   1680
ttcaactggt acgtggacgg cgtggaggtg cataatgcca agacaaagcc gcgagaggag   1740
cagtacaaca gcacgtaccg tgtggtcagc gtcctcaccg tcctgcacca ggactggctg   1800
aatggcaagg agtacaagtg caaggtctcc aacaaagccc tcccagcccc catcgagaaa   1860
accatctcca aagccaaagg gcagccccga gaaccacagg tgtacaccct gcccccatcc   1920
cggaaggaga tgaccaagaa ccaggtcagc ctgacctgcc tggtcaaagg cttctatccc   1980
agcgacatcg ccgtggagtg ggagagcaat gggcagccgg agaacaacta caagaccacg   2040
cctcccgtgc tgaagtccga cggctccttc ttcctctata gcaagctcac cgtggacaag   2100
agcaggtggc agcaggggaa cgtcttctca tgctccgtga tgcatgaggc tctgcacaac   2160
cactacacgc agaagagcct ctccctgtct ccgggtaaag ctgcagcgca tcaccaccac   2220
catcac                                                               2226
```

```
<210> SEQ ID NO 12
<211> LENGTH: 243
<212> TYPE: PRT
<213> ORGANISM: Artificial Sequence
<220> FEATURE:
<223> OTHER INFORMATION: Description of Artificial Sequence: Synthetic
      Amino acid sequence encoding a human IgG1 Fc polypeptide
      containing alterations K392D and K409D, plus L234A and L235A

<400> SEQUENCE: 12
```

His Met Ser Ser Val Ser Ala Gln Ala Ala Glu Pro Lys Ser Ser
1               5                   10                  15

Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu Met
                35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
                100                 105                 110

Lys Glu Tyr Lys Cys Lys Val Ser Asn Lys Ala Leu Pro Ala Pro Ile
            115                 120                 125

Glu Lys Thr Ile Ser Lys Ala Lys Gly Gln Pro Arg Glu Pro Gln Val
    130                 135                 140

Tyr Thr Leu Pro Pro Ser Arg Glu Glu Met Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Asp Thr Thr Pro Pro
            180                 185                 190

Val Leu Asp Ser Asp Gly Ser Phe Phe Leu Tyr Ser Asp Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys

```
<210> SEQ ID NO 13
<211> LENGTH: 729
<212> TYPE: DNA
<213> ORGANISM: Artificial Sequence
<220> FEATURE:
<223> OTHER INFORMATION: Description of Artificial Sequence: Synthetic
      Nucleic acid sequence encoding SEQ ID NO:12

<400> SEQUENCE: 13
```
cacatgtctt cggtaagtgc acaggcggcc gcagagccca aatcttctga caaaactcac      60
acatgcccac cgtgcccagc acctgaagca gctgggggac cgtcagtctt cctcttcccc     120
ccaaaaccca aggacaccct catgatctcc cggacccctg aggtcacatg cgtggtggtg     180
gacgtgagcc acgaagaccc tgaggtcaag ttcaactggt acgtggacgg cgtggaggtg     240
cataatgcca agacaaagcc gcgggaggag cagtacaaca gcacgtaccg tgtggtcagc     300

```
gtcctcaccg tcctgcacca ggactggctg aatggcaagg agtacaagtg caaggtctcc    360
aacaaagccc tcccagcccc catcgagaaa accatctcca aagccaaagg cagccccga    420 gaaccacagg tgtacaccct gccccatcc cgggaggaga tgaccaagaa ccaggtcagc    480
ctgacctgcc tggtcaaagg cttctatccc agcgacatcg ccgtggagtg ggagagcaat    540
gggcagccgg agaacaacta cgacaccacg cctcccgtgc tggactccga cggctccttc    600
ttcctctata gcgacctcac cgtggacaag agcaggtggc agcaggggaa cgtcttctca    660
tgctccgtga tgcatgaggc tctgcacaac cactacacgc agaagagcct ctccctgtct    720
ccgggtaaa                                                            729
```

<210> SEQ ID NO 14
<211> LENGTH: 518
<212> TYPE: PRT
<213> ORGANISM: Artificial Sequence
<220> FEATURE:
<223> OTHER INFORMATION: Description of Artificial Sequence: Synthetic
    Amino acid sequence of a single chain anti-FOLR1/CD3 molecule
    P136637.3 aFOLR1(5G1)scFv-aCD3(F12Q)scFv

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Ser Ser Trp Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Glu Ala Pro Arg Gln Arg Val Thr Ile Ser Cys Ser Gly Ser Ser Ser
145                 150                 155                 160

Asn Ile Gly Asn Asn Ala Val Asn Trp Tyr Gln Gln Leu Pro Gly Lys
                165                 170                 175

Ala Pro Lys Leu Leu Ile Tyr Tyr Asp Asp Met Leu Ser Ser Gly Val
            180                 185                 190

Ser Asp Arg Phe Ser Gly Ser Lys Ser Gly Thr Ser Ala Ser Leu Ala
        195                 200                 205

Ile Ser Gly Leu Gln Ser Glu Asp Glu Ala Asp Tyr Tyr Cys Ala Ala
    210                 215                 220

Trp Asp Asp Ser Leu Asn Gly Val Val Phe Gly Gly Gly Thr Lys Leu
225                 230                 235                 240

Thr Val Leu Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Ser Tyr Ala Met Asn Trp Val Arg Gln
        275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Gly Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
        340                 345                 350

Phe Gly Asn Ser Tyr Val Ser Trp Trp Ala Tyr Trp Gly Gln Gly Thr
        355                 360                 365

Leu Val Thr Val Ser Ser Gly Gly Gly Gly Ser Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Ala Ala Ala Asp Tyr Lys Asp Asp Asp Lys Gly Ser Ser
                500                 505                 510

His His His His His His
        515

<210> SEQ ID NO 15
<211> LENGTH: 742
<212> TYPE: PRT
<213> ORGANISM: Artificial Sequence
<220> FEATURE:
<223> OTHER INFORMATION: Description of Artificial Sequence: Synthetic
      Amino acid sequence of an anti-FOLR1/CD3 Bi-Fc P136635.4
      (aFOLR1(5G1)scFv-aCD3(F12Q)scFv-FcAAKK)

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
        20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Ser Ser Trp Phe Asp Tyr Trp Gly Gln Gly Thr

```
                100              105                110
Leu Val Thr Val Ser Ser Gly Gly Gly Gly Gly Gly Ser
        115              120            125
Gly Gly Gly Gly Ser Gln Ser Val Leu Thr Gln Pro Pro Ser Val Ser
130              135            140
Glu Ala Pro Arg Gln Arg Val Thr Ile Ser Cys Ser Gly Ser Ser Ser
145              150            155            160
Asn Ile Gly Asn Asn Ala Val Asn Trp Tyr Gln Gln Leu Pro Gly Lys
        165              170            175
Ala Pro Lys Leu Leu Ile Tyr Tyr Asp Asp Met Leu Ser Ser Gly Val
        180              185            190
Ser Asp Arg Phe Ser Gly Ser Lys Ser Gly Thr Ser Ala Ser Leu Ala
        195              200            205
Ile Ser Gly Leu Gln Ser Glu Asp Glu Ala Asp Tyr Tyr Cys Ala Ala
        210              215            220
Trp Asp Asp Ser Leu Asn Gly Val Val Phe Gly Gly Gly Thr Lys Leu
225              230            235            240
Thr Val Leu Ser Gly Gly Gly Gly Ser Glu Val Gln Leu Val Glu Ser
        245              250            255
Gly Gly Gly Leu Val Gln Pro Gly Gly Ser Leu Lys Leu Ser Cys Ala
        260              265            270
Ala Ser Gly Phe Thr Phe Asn Ser Tyr Ala Met Asn Trp Val Arg Gln
        275              280            285
Ala Pro Gly Lys Gly Leu Glu Trp Val Ala Arg Ile Arg Ser Lys Tyr
        290              295            300
Asn Asn Tyr Ala Thr Tyr Tyr Ala Asp Ser Val Lys Gly Arg Phe Thr
305              310            315            320
Ile Ser Arg Asp Asp Ser Lys Asn Thr Ala Tyr Leu Gln Met Asn Asn
        325              330            335
Leu Lys Thr Glu Asp Thr Ala Val Tyr Tyr Cys Val Arg His Gly Asn
        340              345            350
Phe Gly Asn Ser Tyr Val Ser Trp Trp Ala Tyr Trp Gly Gln Gly Thr
        355              360            365
Leu Val Thr Val Ser Ser Gly Gly Gly Gly Ser Gly Gly Gly Gly Ser
        370              375            380
Gly Gly Gly Gly Ser Gln Thr Val Val Thr Gln Glu Pro Ser Leu Thr
385              390            395            400
Val Ser Pro Gly Gly Thr Val Thr Leu Thr Cys Gly Ser Ser Thr Gly
        405              410            415
Ala Val Thr Ser Gly Asn Tyr Pro Asn Trp Val Gln Gln Lys Pro Gly
        420              425            430
Gln Ala Pro Arg Gly Leu Ile Gly Gly Thr Lys Phe Leu Ala Pro Gly
        435              440            445
Thr Pro Ala Arg Phe Ser Gly Ser Leu Leu Gly Gly Lys Ala Ala Leu
        450              455            460
Thr Leu Ser Gly Val Gln Pro Glu Asp Glu Ala Glu Tyr Tyr Cys Val
465              470            475            480
Leu Trp Tyr Ser Asn Arg Trp Val Phe Gly Gly Gly Thr Lys Leu Thr
        485              490            495
Val Leu Ala Ala Ala Glu Pro Lys Ser Ser Asp Lys Thr His Thr Cys
        500              505            510
Pro Pro Cys Pro Ala Pro Glu Ala Ala Gly Gly Pro Ser Val Phe Leu
        515              520            525
```

Phe Pro Pro Lys Pro Lys Asp Thr Leu Met Ile Ser Arg Thr Pro Glu
    530                 535                 540

Val Thr Cys Val Val Val Asp Val Ser His Glu Asp Pro Glu Val Lys
545                 550                 555                 560

Phe Asn Trp Tyr Val Asp Gly Val Glu Val His Asn Ala Lys Thr Lys
                565                 570                 575

Pro Arg Glu Glu Gln Tyr Asn Ser Thr Tyr Arg Val Val Ser Val Leu
            580                 585                 590

Thr Val Leu His Gln Asp Trp Leu Asn Gly Lys Glu Tyr Lys Cys Lys
        595                 600                 605

Val Ser Asn Lys Ala Leu Pro Ala Pro Ile Glu Lys Thr Ile Ser Lys
    610                 615                 620

Ala Lys Gly Gln Pro Arg Glu Pro Gln Val Tyr Thr Leu Pro Pro Ser
625                 630                 635                 640

Arg Lys Glu Met Thr Lys Asn Gln Val Ser Leu Thr Cys Leu Val Lys
                645                 650                 655

Gly Phe Tyr Pro Ser Asp Ile Ala Val Glu Trp Glu Ser Asn Gly Gln
            660                 665                 670

Pro Glu Asn Asn Tyr Lys Thr Thr Pro Pro Val Leu Lys Ser Asp Gly
        675                 680                 685

Ser Phe Phe Leu Tyr Ser Lys Leu Thr Val Asp Lys Ser Arg Trp Gln
    690                 695                 700

Gln Gly Asn Val Phe Ser Cys Ser Val Met His Glu Ala Leu His Asn
705                 710                 715                 720

His Tyr Thr Gln Lys Ser Leu Ser Leu Ser Pro Gly Lys Ala Ala Ala
                725                 730                 735

His His His His His His
            740

<210> SEQ ID NO 16
<211> LENGTH: 2226
<212> TYPE: DNA
<213> ORGANISM: Artificial Sequence
<220> FEATURE:
<223> OTHER INFORMATION: Description of Artificial Sequence: Synthetic
      Nucleic acid sequence encoding SEQ ID NO:15 (aFOLR1(5G1)scFv-
      aCD3(F12Q)scFv-FcAAKK)

<400> SEQUENCE: 16
caggtgcagc tgcaggagtc gggcccagga ctggtgaagc cttcacagac cctgtccctc      60
acctgcactg tctctggtgg ctccatcagc agtggtgctt actactggac ctggatccgc     120
cagcacccag ggaagggcct ggagtggatt gggtacatct attacagtgg gagcacctac     180
tacaacccgt ccctcaagag tcgagttagc atatcaatag acacgtctaa gaaccagttc     240
tccctgaagc tgagctctgt gactgccgcg gacacggccg tgtattactg cgcgagggc     300 agcagcagct ggttcgacta ctggggccag gaaccctgg tcaccgtctc ctcaggaggc     360
ggcggttcag gcggaggtgg ctctggcggt ggcggaagtc agtctgtgct gactcagcca     420
ccctcggtgt ctgaagcccc caggcagagg gtcaccatct cctgttctgg aagcagctcc     480
aacatcggaa ataatgctgt aaactggtac cagcagctcc caggaaaggc tcccaaactc     540
ctcatctatt atgatgatat gttgtcttca ggggtctcgg accgattttc tggctccaag     600
tctggcacct cagcctccct ggccatcagt gggctccagt ctgaggatga ggctgattat     660
tactgtgcag catgggatga cagcctgaat ggtgtggtat tcggcggagg gaccaagctg     720

```
accgtcctat ccggaggtgg tggatccgag gtgcagctgg tcgagtctgg aggaggattg    780
gtgcagcctg gagggtcatt gaaactctca tgtgcagcct ctggattcac cttcaatagc    840
tacgccatga actgggtccg ccaggctcca ggaaagggtt tggaatgggt tgctcgcata    900
agaagtaaat ataataatta tgcaacatat tatgccgatt cagtgaaagg caggttcacc    960
atctccagag atgattcaaa aaacactgcc tatctacaaa tgaacaactt gaaaactgag   1020
gacactgccg tgtactactg tgtgagacat gggaacttcg gtaatagcta cgtttcctgg   1080
tgggcttact ggggccaagg gactctggtc accgtctcct caggtggtgg tggttctggc   1140
ggcggcggct ccgtggtggg tggttctcag actgttgtga ctcaggaacc ttcactcacc   1200
gtatcacctg gtggaacagt cacactcact tgtggctcct cgactgggc tgttacatct    1260
ggcaactacc caaactgggt ccaacaaaaa ccaggtcagg caccccgtgg tctaataggt   1320
gggactaagt tcctcgcccc cggtactcct gccagattct caggctccct gcttggaggc   1380
aaggctgccc tcaccctctc aggggtacag ccagaggatg aggcagaata ttactgtgtt   1440
ctatggtaca gcaaccgctg ggtgttcggt ggaggaacca aactgactgt cctagcggcc   1500
gcagagccca atcttctga caaaactcac acatgccccc cgtgcccagc acctgaagca    1560
gctggggac cgtcagtctt cctcttcccc ccaaaaccca aggacaccct catgatctcc    1620
cggacccctg aggtcacatg cgtggtggtg gacgtgagcc acgaagaccc tgaggtcaag   1680
ttcaactggt acgtggacgg cgtggaggtg cataatgcca agacaaagcc gcgagaggag   1740
cagtacaaca gcacgtaccg tgtggtcagc gtcctcaccg tcctgcacca ggactggctg   1800
aatggcaagg agtacaagtg caaggtctcc aacaaagccc tcccagcccc catcgagaaa   1860
accatctcca aagccaaagg gcagccccga gaaccacagg tgtacaccct gcccccatcc   1920
cggaaggaga tgaccaagaa ccaggtcagc ctgacctgcc tggtcaaagg cttctatccc   1980
agcgacatcg ccgtggagtg ggagagcaat gggcagccgg agaacaacta caagaccacg   2040
cctcccgtgc tgaagtccga cggctccttc ttcctctata gcaagctcac cgtggacaag   2100
agcaggtggc agcaggggaa cgtcttctca tgctccgtga tgcatgaggc tctgcacaac   2160
cactacacgc agaagagcct ctccctgtct ccgggtaaag ctgcagcgca tcaccaccac   2220
catcac                                                              2226
```

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Val Ala Ala Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

Ala Ser Thr Lys Gly Pro
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 19

```
Gly Gly Gly Gly Ser Gly Gly Gly Gly Ser
1               5                   10
```

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 20

```
Gly Gly Gly Gly Ser Ala Ala Ala
1               5
```

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 21

```
Gly Gly Gly Gly Ser Gly Gly Gly Gly Ser Gly Gly Gly Gly Ser
1               5                   10                  15
```

<210> SEQ ID NO 22
<211> LENGTH: 186
<212> TYPE: PRT
<213> ORGANISM: Homo sapiens
<220> FEATURE:
<221> NAME/KEY: MISC_FEATURE
<223> OTHER INFORMATION: Mature amino acid sequence of CD3 epsilon chain
      of Homo sapiens

<400> SEQUENCE: 22

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
            35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125
```

-continued

```
Tyr Trp Ser Lys Asn Arg Lys Ala Lys Ala Lys Pro Val Thr Arg Gly
        130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Ile
            180                 185

<210> SEQ ID NO 23
<211> LENGTH: 177
<212> TYPE: PRT
<213> ORGANISM: Macaca fascicularis
<220> FEATURE:
<221> NAME/KEY: MISC_FEATURE
<223> OTHER INFORMATION: Mature amino acid sequence of CD3 epsilon chain
      of Macaca fascicularis

<400> SEQUENCE: 23

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
                20                  25                  30

Gly Ser Glu Ala Gln Trp Gln His Asn Gly Lys Asn Lys Gly Asp Ser
            35                  40                  45

Gly Asp Gln Leu Phe Leu Pro Glu Phe Ser Glu Met Glu Gln Ser Gly
        50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

Val Met Ala Val Ala Thr Ile Val Ile Val Asp Ile Cys Ile Thr Leu
                100                 105                 110

Gly Leu Leu Leu Leu Val Tyr Tyr Trp Ser Lys Asn Arg Lys Ala Lys
            115                 120                 125

Ala Lys Pro Val Thr Arg Gly Ala Gly Ala Gly Gly Arg Gln Arg Gly
        130                 135                 140

Gln Asn Lys Glu Arg Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide which is a portion of an epitope of CD3 epsilon

<400> SEQUENCE: 24

Gln Asp Gly Asn Glu
1               5

<210> SEQ ID NO 25
<211> LENGTH: 232
<212> TYPE: PRT
<213> ORGANISM: Homo sapiens
<220> FEATURE:
```

<221> NAME/KEY: MISC_FEATURE
<223> OTHER INFORMATION: Amino acid sequence of human IgG1 Fc region

<400> SEQUENCE: 25

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 26
<211> LENGTH: 228
<212> TYPE: PRT
<213> ORGANISM: Homo sapiens
<220> FEATURE:
<221> NAME/KEY: MISC_FEATURE
<223> OTHER INFORMATION: Amino acid sequence of human IgG2 Fc region

<400> SEQUENCE: 26

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Met Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 27
<211> LENGTH: 279
<212> TYPE: PRT
<213> ORGANISM: Homo sapiens
<220> FEATURE:
<221> NAME/KEY: MISC_FEATURE
<223> OTHER INFORMATION: Amino acid sequence of human IgG3 Fc region

<400> SEQUENCE: 27

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

```
Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 28
<211> LENGTH: 229
<212> TYPE: PRT
<213> ORGANISM: Homo sapiens
<220> FEATURE:
<221> NAME/KEY: MISC_FEATURE
<223> OTHER INFORMATION: Amino acid sequence of human IgG4 Fc region

<400> SEQUENCE: 28

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 29
<211> LENGTH: 125
<212> TYPE: PRT
<213> ORGANISM: Artificial Sequence
<220> FEATURE:
<223> OTHER INFORMATION: Description of Artificial Sequence: Synthetic
      Amino acid sequence of an anti-CD3-epsilon VH region (12C)

<400> SEQUENCE: 29
```

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 30
<211> LENGTH: 375
<212> TYPE: DNA
<213> ORGANISM: Artificial Sequence
<220> FEATURE:
<223> OTHER INFORMATION: Description of Artificial Sequence: Synthetic
      Nucleic acid sequence encoding SEQ ID NO:29

<400> SEQUENCE: 30
gaggtgcagc tggtcgagtc tggaggagga ttggtgcagc ctggagggtc attgaaactc      60
tcatgtgcag cctctggatt caccttcaat aagtacgcca tgaactgggt ccgccaggct     120
ccaggaaagg gtttggaatg ggttgctcgc ataagaagta atataataa ttatgcaaca     180 tattatgccg attcagtgaa agacaggttc accatctcca gagatgattc aaaaaacact     240
gcctatctac aaatgaacaa cttgaaaact gaggacactg ccgtgtacta ctgtgtgaga     300
catgggaact tcggtaatag ctacatatcc tactgggctt actggggcca agggactctg     360
gtcaccgtct cctca                                                     375

<210> SEQ ID NO 31
<211> LENGTH: 109
<212> TYPE: PRT
<213> ORGANISM: Artificial Sequence
<220> FEATURE:
<223> OTHER INFORMATION: Description of Artificial Sequence: Synthetic
      Amino acid sequence of an anti-CD3-epsilon VL region (12C)

<400> SEQUENCE: 31

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 32
<211> LENGTH: 327
<212> TYPE: DNA
<213> ORGANISM: Artificial Sequence
<220> FEATURE:
<223> OTHER INFORMATION: Description of Artificial Sequence: Synthetic
      Nucleic acid sequence encoding SEQ ID NO:31

<400> SEQUENCE: 32
cagactgttg tgactcagga accttcactc accgtatcac ctggtggaac agtcacactc    60
acttgtggct cctcgactgg ggctgttaca tctggcaact acccaaactg ggtccaacaa   120
aaaccaggtc aggcaccccg tggtctaata ggtgggacta agttcctcgc ccccggtact   180
cctgccagat tctcaggctc cctgcttgga ggcaaggctg ccctcaccct ctcagggta    240 cagccagagg atgaggcaga atattactgt gttctatggt acagcaaccg ctgggtgttc   300
ggtggaggaa ccaaactgac tgtccta                                       327

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Cys Val Phe Asn Met Phe Asn Cys Gly Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Cys His Leu Pro Phe Ala Val Cys Gly Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Cys Gly His Glu Tyr Met Trp Cys Gly Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Gly Gly Cys Trp Pro Leu Gln Asp Tyr Cys Gly Gly
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Gly Gly Cys Met Gln Met Asn Lys Trp Cys Gly Gly
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gly Gly Cys Asp Gly Arg Thr Lys Tyr Cys Gly Gly
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Gly Gly Cys Ala Leu Tyr Pro Thr Asn Cys Gly Gly
1               5                   10
```

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gly Gly Cys Gly Lys His Trp His Gln Cys Gly Gly
1               5                   10
```

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Gly Gly Cys His Ser Phe Lys His Phe Cys Gly Gly
1               5                   10
```

<210> SEQ ID NO 42
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 42

Gly Gly Cys Gln Gly Met Trp Thr Trp Cys Gly Gly
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Cys Ala Gln Gln Trp His His Glu Tyr Cys Gly Gly
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Cys Glu Arg Phe His His Ala Cys Gly Gly
1               5                   10
```

BISPECIFIC-FC MOLECULES

CROSS REFERENCE TO RELATED APPLICATIONS

This application is a continuation of U.S. patent application Ser. No. 14/210,178, filed Mar. 13, 2014, now abandoned, which claims the benefit of U.S. Provisional Application 61/791,424, filed Mar. 15, 2013, the content of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 11, 2014, is named A-1810-US-NP_SL.txt and is 58,831 bytes in size.

BACKGROUND

Bispecific antibodies have promise as therapeutics in a variety of indications. Bispecific antibodies having a standard IgG format can be challenging to produce because they include four different polypeptide chains. The efficacy of a smaller, more easily-produced bispecific molecule has been clinically demonstrated in non-Hodgkin's lymphoma. See, e.g., Bargou et al. (2008), Science 321(5891): 974-977. Daily administration was used to achieve these results, presumably because of the short in vivo half life of this small, single chain molecule. Id Hence, there is a need in the art for bispecific therapeutics with favorable pharmacokinetic properties, as well as therapeutic efficacy and a format that makes them straightforward to produce.

SUMMARY

A Bispecific-Fc (Bi-Fc) as described herein molecule can bind to one molecule of each of two different proteins and contains an Fc region of an antibody. A Bi-Fc also can have favorable pharmacokinetic properties relative to a single chain molecule lacking an Fc region. One protein bound by a Bi-Fc can be expressed on an immune effector cell such as a T cell, an NK cell, a neutrophil, or a macrophage, and the other protein can be expressed on a target cell, for example, a cancer cell, a cell infected by a pathogen, or a cell mediating a disease, such as a fibrotic cell. The Bi-Fc molecules described herein can elicit activation an immune effector cell in the presence of a target cell.

In one aspect, provided herein is a Bi-Fc, which can comprise: (a) (i) a first polypeptide chain having the formula V1-L1-V2-L2-V3-L3-V4-L4-Fc, wherein Fc is an Fc polypeptide chain, wherein V1, V2, V3, and V4 are each immunoglobulin variable regions that have different amino acid sequences, wherein L1, L2, L3, and L4 are linkers, and wherein L4 can be present or absent, and (ii) a second polypeptide chain that comprises an Fc polypeptide chain; or (b) (i) a first polypeptide chain having the formula Fc-L4-V1-L1-V2-L2-V3-L3-V4, wherein Fc is an Fc polypeptide chain, wherein V1, V2, V3, and V4 are each immunoglobulin variable regions that have different amino acid sequences, wherein L1, L2, L3, and L4 are linkers, and wherein L4 can be present or absent, and (ii) a second polypeptide chain that comprises an Fc polypeptide chain; wherein the Bi-Fc mediates cytolysis of a target cell displaying a target cell protein by an immune effector cell, and does not mediate cytolysis of a cell not displaying the target cell protein by the immune effector cell and/or wherein the Bi-Fc can bind to a target cell and to an immune effector cell. V1 can be a heavy chain variable (VH) region, and V2 can be a light chain variable (VL) region. In an alternate embodiment, V1 can be a VL region and V2 can be a VH region. V3 and V4 can be a VH and a VL region, respectively, or V3 and V4 can be a VL and a VH region, respectively. L1 and L3 can be at least 15 amino acids long, and L2 can be less than 12 amino acids long. V1 and V2 can bind to a target cell or an immune effector cell when they are part of an IgG and/or an scFv antibody, and V3 and V4 can bind to a target cell or an immune effector cell when they are part of an IgG and/or an scFv antibody. The Fc polypeptide chain in the first polypeptide chain can comprise a heterodimerizing alteration, and the Fc polypeptide chain in the second polypeptide chain can comprise another heterodimerizing alteration. The heterodimerizing alteration in the first polypeptide chain can be a charge pair substitution, and the heterodimerizing alteration in the second polypeptide chain can be a charge pair substitution. The first polypeptide chain can comprise the charge pair substitutions K409D or K409E and K392D or K392E, and the second polypeptide chain can comprise the charge pair substitutions D399K or D399R and D356K or D356R; or the second polypeptide chain comprises the charge pair substitutions K409D or K409E and K392D or K392E, and the first polypeptide chain comprises the charge pair substitutions D399K or D399R and D356K or D356R. The Fc polypeptide chains of the first and second polypeptide chains can be human IgG Fc polypeptide chains, such as IgG1, IgG2, IgG3, or IgG4 Fc polypeptide chains. The Fc polypeptide chains of the first and second polypeptide chains can comprise one or more alterations that inhibit(s) Fc gamma receptor (FcγR) binding or enhance(s) ADCC. The Fc polypeptide chains of the first and second polypeptide chains comprise, for example, L234A, L235A, and any substitution at N297.

In a further aspect, described herein is a Bi-Fc, which can comprise: (i) a first polypeptide chain having following formula: V1-L1-V2-L2-V3-L3-V4-L4-Fc, wherein Fc is an Fc polypeptide chain, wherein V1, V2, V3, and V4 are each immunoglobulin variable regions that have different amino acid sequences, wherein L1, L2, L3, and L4 are linkers, and wherein L4 can be present or absent; and (ii) a second polypeptide chain comprising an Fc polypeptide chain; wherein L1 and L3 are at least 15 amino acids long and L2 is less than 12 amino acids long; wherein either V1 is a VH region and V2 is a VL region or V1 is a VL region and V2 is a VH region; wherein either V3 is a VH region and V4 is a VL region or V3 is a VL region and V4 is a VH region; wherein the Fc polypeptide chains of each of the first and second polypeptide chains each contain a heterodimerizing alteration; and wherein the Bi-Fc mediates cytolysis of a target cell displaying a target cell protein by an immune effector cell, and does not mediate cytolysis of a cell not displaying the target cell protein by the immune effector cell, and/or the Bi-Fc can bind to a target cell and to an immune effector cell. The Fc polypeptide chains can be human IgG Fc polypeptide chains, such as IgG1, IgG2, IgG3, or IgG4 Fc polypeptide chains. The Fc polypeptide chains of the first and second polypeptide chains comprise one or more alteration that inhibits FcγR binding, such as one or more of L234A, L235A, and any substitution at N297.

In a further aspect, a Bi-Fc can comprise: (a) a first polypeptide chain having the formula V1-L1-V2-L2-V3-L3-V4-L4-Fc, wherein Fc is an Fc polypeptide chain, wherein V1, V2, V3, and V4 are each immunoglobulin variable regions that have different amino acid sequences, wherein L1, L2, L3, and L4 are linkers, and wherein L4 can be present or absent; or (b) a first polypeptide chain having the following formula: Fc-L4-V1-L1-V2-L2-V3-L3-V4, wherein Fc is an Fc polypeptide chain, wherein V1, V2, V3, and V4 are each immunoglobulin variable regions that have different amino acid sequences, wherein L1, L2, L3, and L4 are linkers, and wherein L4 can be present or absent; wherein the Bi-Fc is a monomer and wherein the Bi-Fc mediates cytolysis of a target cell displaying a target cell protein by an immune effector cell, and does not mediate cytolysis of a cell not displaying the target cell protein by the immune effector cell, and/or the Bi-Fc can bind to a target cell and to an immune effector cell. The Fc polypeptide chain can be a human IgG Fc polypeptide chain, such as IgG1, IgG2, IgG3, or IgG4 Fc polypeptide chain. The Fc polypeptide chain of (a) or (b) can comprise one or more the following alterations: K392D, K382E, K409D, K409E, Y349T, L351T, L368T, L398T, F405T, Y407T, Y407R. The Fc polypeptide chain of (a) or (b) can comprise one or more alteration that inhibits FcγR binding, such as one or more of L234A, L235A, and any substitution at N297.

The immune effector cell of any Bi-Fc described herein can be a human T cell and/or a cynomolgus monkey T cell. The effector cell protein of any Bi-Fc described herein can be part of the human and/or cynomolgus monkey TCR-CD3 complex. The effector cell protein of any Bi-Fc described herein can be the human and/or cynomolgus monkey TCRα, TCRβ, TCRγ, TCRδ, CD3β chain, CD3γ chain, CD3δ chain, CD3ε chain, or CD3ζ chain.

If the effector cell protein is the CD3ε chain, the Bi-Fc can comprise a VH region and a VL comprising the amino acid sequences of SEQ ID NOs:7 and 8, respectively, or comprising the amino acid sequences of SEQ ID NOs:29 and 31, respectively.

The target cell of any Bi-Fc can be a cancer cell, a cell infected by a pathogen, or a cell that mediates disease. If target cell is a cancer cell, the cancer can be a hematologic malignancy or a solid tumor malignancy. If the target cell is a cell infected by a pathogen, the pathogen can be virus, including human immunodeficiency virus, hepatitis virus, human papilloma virus, or cytomegalovirus, or a bacterium of the genus *Listeria, Mycobacterium, Staphylococcus*, or *Streptococcus*. If the target cell is a cell that mediates a disease, the target cell can be a fibrotic cell that mediates a fibrotic disease or an autoimmune or inflammatory disease.

Provided herein is pharmaceutical formulation comprising any of the Bi-Fc molecules described herein and a physiologically acceptable excipient.

Further provided herein are nucleic acids encoding any of the Bi-Fc described herein and vectors containing such nucleic acids, as well as host cell containing such nucleic acids and/or vectors. In another aspect, described herein is a method for making a Bi-Fc comprising culturing the host cell containing the nucleic acids or vector under conditions such that the nucleic acids are expressed, and recovering the Bi-Fc from the cell mass or the culture medium.

In another aspect, provided herein is a method for treating a cancer patient comprising administering to the patient a therapeutically effective dose of any of the Bi-Fc molecules described herein, wherein the target cell of the Bi-Fc is a cancer cell. This method can further comprise administering radiation, a chemotherapeutic agent, or a non-chemotherapeutic, anti-neoplastic agent before, after, or concurrently with the administration of the Bi-Fc. The patient can have a hematologic malignancy or a solid tumor malignancy.

In a further embodiment, described herein is a method for treating a patient having a fibrotic disease comprising administering to the patient a therapeutically effective dose of any of the Bi-Fc molecules described herein, wherein the target cell of the Bi-Fc is a fibrotic cell. The fibrotic disease can be atherosclerosis, chronic obstructive pulmonary disease (COPD), cirrhosis, scleroderma, kidney transplant fibrosis, kidney allograft nephropathy, or a pulmonary fibrosis, including idiopathic pulmonary fibrosis.

In still another aspect, described herein is a method for treating a patient having a disease mediated by a pathogen comprising administering to the patient a therapeutically effective dose of any of the Bi-Fc molecules described herein. The pathogen can be a virus, a bacterium, or a protozoan.

Also provided herein is a pharmaceutical composition comprising any of the Bi-Fc molecules described herein. Such compositions can be for the treatment of a cancer, an infectious disease, an autoimmune or inflammatory disease, or a fibrotic disease.

BRIEF DESCRIPTION OF THE FIGURES

FIG. 5A (panel A) shows data for interferon gamma (IFNγ). FIG. 5A (panel B) shows data for tumor necrosis factor alpha (TNFα). FIG. 5A (panel C) shows data for interleukin-10 (IL-10). FIG. 5B (panel D) shows data for interleukin-2 (IL-2). FIG. 5B (panel E) shows data for interleukin-13 (IL-13). As indicated, graphs on the left show data from T47D cells (which express FOLR1), and graphs on the right show data from BT474 cells (which do not express FOLR1).

FIG. 6A (panels A, B, and C) and FIG. 6B (panels D and E) show data for IFNγ, TNFα, IL-10, IL-2, and IL-13, respectively, as indicated. As indicated, panels on the left show data from JIMT-1 cells (which express HER2), and panels on the right show data from SHP77 cells (which do not express HER2).

BRIEF DESCRIPTION OF THE SEQUENCES

Figure 1:
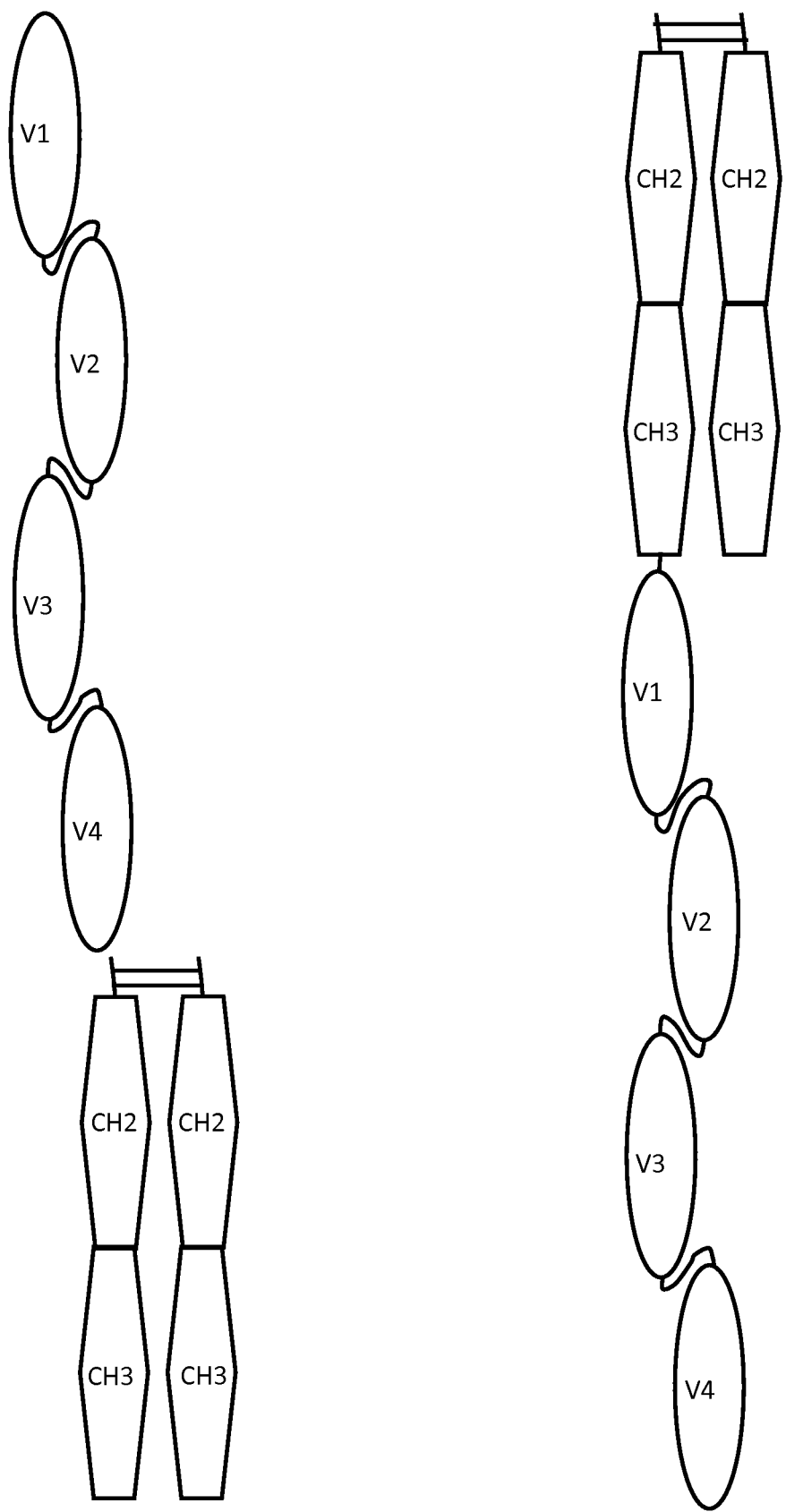
FIG. 1: A diagram of a Bi-Fc molecule. Four immunoglobulin variable regions are indicated by ovals and labeled V1, V2, V3, and V4. CH2 and CH3 regions are labeled as such and diagramed as an elongated hexagon. Lines between these regions indicate linkers or a hinge region. Exemplary disulfide bridges are indicated by horizontal lines.

| SEQ ID NO | Description |
|---|---|
| SEQ ID NO: 1 | Amino acid sequence preceding VH CDR1 |
| SEQ ID NO: 2 | Amino acid sequence preceding VH CDR2 |
| SEQ ID NO: 3 | Amino acid sequence following VH CDR3 |

-continued

| SEQ ID NO | Description |
|---|---|
| SEQ ID NO: 4 | Amino acid sequence following light chain CDR3 |
| SEQ ID NO: 5 | Amino acid sequence of anti-HER2 VH region |
| SEQ ID NO: 6 | Amino acid sequence of anit-HER2 VL region |
| SEQ ID NO: 7 | Amino acid sequence of anti CD3ε VH region |
| SEQ ID NO: 8 | Amino acid sequence of anti-CD3ε VL region |
| SEQ ID NO: 9 | Amino acid sequence of a single chain anti-HER2/CD3 (P136629.3) |
| SEQ ID NO: 10 | Amino acid sequence of a first polypeptide chain of an anti-HER2/CD3 of a Bi-Fc |
| SEQ ID NO: 11 | Nucleic acid sequence of SEQ ID NO: 10 |
| SEQ ID NO: 12 | Amino acid sequence of a human IgG1 Fc polypeptide containing alterations D356K and D399K |
| SEQ ID NO: 13 | Nucleic acid sequence encoding SEQ ID NO: 12 |
| SEQ ID NO: 14 | Amino acid sequence of ao single chain anti-FOLR1/CD3 molecule |
| SEQ ID NO: 15 | Amino acid sequence of a first polypeptide chain of an anti-FOLR1/CD3 molecule |
| SEQ ID NO: 16 | Nucleic acid sequence encoding SEQ ID NO: 15 |
| SEQ ID NO: 17 | Amino acid sequence of a linker |
| SEQ ID NO: 18 | Amino acid sequence of a linker |
| SEQ ID NO: 19 | Amino acid sequence of a linker |
| SEQ ID NO: 20 | Amino acid sequence of a linker |
| SEQ ID NO: 21 | Amino acid sequence of a linker |
| SEQ ID NO: 22 | Mature amino acid sequence of CD3 epsilon chain of *Homo sapiens* |
| SEQ ID NO: 23 | Mature amino acid sequence of CD3 epsilon chain of *Macaca fascicularis* |
| SEQ ID NO: 24 | A portion of an epitope that is part of CD3 epsilon |
| SEQ ID NO: 25 | Amino acid sequence of human IgG1 Fc region |
| SEQ ID NO: 26 | Amino acid sequence of human IgG2 Fc region |
| SEQ ID NO: 27 | Amino acid sequence of human IgG3 Fc region |
| SEQ ID NO: 28 | Amino acid sequence of human IgG4 Fc region |
| SEQ ID NO: 29 | Amino acid sequence of an anti-CD3ε VH region |
| SEQ ID NO: 30 | Nucleic acid sequence encoding SEQ ID NO: 29 |
| SEQ ID NO: 31 | Amino acid sequence of an anti-CD3ε VL region |
| SEQ ID NO: 32 | Nucleic acid sequence encoding SEQ ID NO: 31 |

DETAILED DESCRIPTION

Described is a new form of bispecific antibody, called herein a Bi-Fc, which contains one polypeptide chain or two different polypeptide chains. One chain comprises two heavy chain variable (VH) regions, two light chain variable (VL) regions, and an Fc polypeptide chain, and an optional second polypeptide chain comprises an Fc polypeptide chain. In some embodiments, one of the proteins to which the Bi-Fc binds is expressed on the surface of an immune effector cell, such as a T cell, an NK cell, a macrophage, or a neutrophils, and the other protein to which the Bi-Fc binds is expressed on the surface of a target cell, for example a cancer cell, a cell infected by a pathogen, or a cell that mediates a disease, such as, for example, a fibrotic disease. Since a Bi-Fc has only one binding site for each of these proteins (i.e., it binds each protein "monovalently," as meant herein), its binding, by itself, will not oligomerize the proteins it binds to on a cell surface. For example, if it binds to CD3 on the surface of a T cell, CD3 will not be oligomerized on the T cell surface in the absence of a target cell. Oligomerization of CD3 can cause a generalized activation of a T cell, which can be undesirable. The Bi-Fc tethers an immune effector cell to a target cell, thereby eliciting specific cytolytic activity against the target cell, rather than a generalized inflammatory response. Further, the Bi-Fc molecules have favorable pharmacokinetic properties and are not unduly complex to manufacture since they contain only one or only two different polypeptide chains.

Definitions

An "antibody," as meant herein, is a protein containing at least one VH or VL region, in many cases a heavy and a light chain variable region. Thus, the term "antibody" encompasses molecules having a variety of formats, including single chain Fv antibodies (scFv, which contain VH and VL regions joined by a linker), Fab, F(ab)₂', Fab', scFv:Fc antibodies (as described in Carayannopoulos and Capra, Ch. 9 in FUNDAMENTAL IMMUNOLOGY, 3$^{rd}$ ed., Paul, ed., Raven Press, New York, 1993, pp. 284-286) or full length antibodies containing two full length heavy and two full length light chains, such as naturally-occurring IgG antibodies found in mammals. Id. Such IgG antibodies can be of the IgG1, IgG2, IgG3, or IgG4 isotype and can be human antibodies. The portions of Carayannopoulos and Capra that describe the structure of antibodies are incorporated herein by reference. Further, the term "antibody" includes dimeric antibodies containing two heavy chains and no light chains such as the naturally-occurring antibodies found in camels and other dromedary species and sharks. See, e.g., Muldermans et al., 2001, J. Biotechnol. 74:277-302; Desmyter et al., 2001, J. Biol. Chem. 276:26285-90; Streltsov et al. (2005), Protein Science 14: 2901-2909. An antibody can be "monospecific" (that is, binding to only one kind of antigen), "bispecific" (that is, binding to two different antigens), or "multispecific" (that is, binding to more than one different antigen). Further, an antibody can be monovalent, bivalent, or multivalent, meaning that it can bind to one, two, or multiple antigen molecules at once, respectively. An antibody binds "monovalently" to a particular protein when one molecule of the antibody binds to only one molecule of the protein, even though the antibody may also bind to a different protein as well. That is, an antibody binds "monovalently," as meant herein, to two different proteins when it binds to only one molecule of each protein. Such an antibody is "bispecific" and binds to each of two different proteins "monovalently." An antibody can be "monomeric," i.e., comprising a single polypeptide chain. An antibody can comprise multiple polypeptide chains ("multimeric") or can comprise two ("dimeric"), three ("trimeric"), or four ("tetrameric") polypeptide chains. If multimeric, an antibody can be a homomulitmer, i.e., containing more than one molecule of only one kind of polypeptide chain, including homodimers, homotrimer, or homotetramers. Alternatively, a multimeric antibody can be a heteromultimer, i.e., containing more than one different kind of polypeptide chain, including heterodimers, heterotrimers, or heterotetramers. An antibody can have a variety of possible formats including, for example, monospecific monovalent antibodies (as described in International Application WO 2009/089004 and US Publication 2007/0105199, the relevant portions of which are incorporated herein by reference) that may inhibit or activate the molecule to which they bind, bivalent monospecific or bispecific dimeric Fv-Fc, scFv-Fc, or diabody Fc, monospecific monovalent scFv-Fc/Fc's, the multispecific binding proteins and dual variable domain immunoglobulins described in US Publication 2009/0311253 (the relevant portions of which are incorporated herein by reference), the heterodimeric bispecific antibodies described herein, and the many formats for bispecific antibodies described in Chapters 1, 4, 5, 6, 7, 8, 9, 10, 11, 12, 13, 14 of BISPECIFIC ANTIBODIES, Kontermann, ed., Springer, 2011 (which chapters are incorporated herein by reference), among many other possible antibody formats.

A "Bi-Fc," as meant herein, comprises a first polypeptide chain and, optionally, a second polypeptide chain. In many embodiments, a Bi-Fc comprises both a first and a second polypeptide chain. In some embodiments, a Bi-Fc is a monomer comprising only the first polypeptide chain. The first polypeptide chain comprises two VH regions and two VL regions separated by linkers and an Fc polypeptide chain. The Fc polypeptide chain can be N-terminal or C-terminal relative to the four immunoglobulin variable regions, and it can be joined to the variable regions via a linker. This linker can be present or absent. The second polypeptide chain, if present, comprises an Fc polypeptide chain. Thus, a Bi-Fc can be a monomer or a heterodimer. A Bi-Fc can bind to an immune effector cell via an effector cell protein and to a target cell via a target cell protein and can mediate cytolysis of a target cell by an immune effector cell.

A "cancer cell antigen," as meant herein, is a protein expressed on the surface of a cancer cell. Some cancer cell antigens are also expressed on some normal cells, and some are specific to cancer cells. Cancer cell antigens can be highly expressed on the surface of a cancer cell. There are a wide variety of cancer cell antigens. Examples of cancer cell antigens include, without limitation, the following human proteins: epidermal growth factor receptor (EGFR), EGFRvIII (a mutant form of EGFR), melanoma-associated chondroitin sulfate proteoglycan (MCSP), mesothelin (MSLN), folate receptor 1 (FOLR1), and human epidermal growth factor 2 (HER2), among many others.

"Chemotherapy," as used herein, means the treatment of a cancer patient with a "chemotherapeutic agent" that has cytotoxic or cytostatic effects on cancer cells. A "chemotherapeutic agent" specifically targets cells engaged in cell division and not cells that are not engaged in cell division. Chemotherapeutic agents directly interfere with processes that are intimately tied to cell division such as, for example, DNA replication, RNA synthesis, protein synthesis, the assembly, disassembly, or function of the mitotic spindle, and/or the synthesis or stability of molecules that play a role in these processes, such as nucleotides or amino acids. A chemotherapeutic agent therefore has cytotoxic or cytostatic effects on both cancer cells and other cells that are engaged in cell division. Chemotherapeutic agents are well-known in the art and include, for example: alkylating agents (e.g. busulfan, temozolomide, cyclophosphamide, lomustine (CCNU), methyllomustine, streptozotocin, cis-diamminedichloroplatinum, aziridinylbenzo-quinone, and thiotepa); inorganic ions (e.g. cisplatin and carboplatin); nitrogen mustards (e.g. melphalan hydrochloride, ifosfamide, chlorambucil, and mechlorethamine HCl); nitrosoureas (e.g. carmustine (BCNU)); anti-neoplastic antibiotics (e.g. adriamycin (doxorubicin), daunomycin, mitomycin C, daunorubicin, idarubicin, mithramycin, and bleomycin); plant derivatives (e.g. vincristine, vinblastine, vinorelbine, paclitaxel, docetaxel, vindesine, VP-16, and VM-26); antimetabolites (e.g. methotrexate with or without leucovorin, 5-fluorouracil with or without leucovorin, 5-fluorodeoxyuridine, 6-mercaptopurine, 6-thioguanine, cytarabine, 5-azacytidine, hydroxyurea, deoxycoformycin, gemcitabine, and fludarabine); podophyllotoxins (e.g. etoposide, irinotecan, and topotecan); as well as actinomycin D, dacarbazine (DTIC), mAMSA, procarbazine, hexamethylmelamine, pentamethylmelamine, L-asparaginase, and mitoxantrone, among many known in the art. See e.g. Cancer: Principles and Practice of Oncology, 4$^{th}$ Edition, DeVita et al., eds., J.B. Lippincott Co., Philadelphia, Pa. (1993), the relevant portions of which are incorporated herein by reference. Alkylating agents and nitrogen mustard act by alkylating DNA, which restricts uncoiling and replication of strands. Methotrexate, cytarabine, 6-mercaptopurine, 5-fluorouracil, and gemcitabine interfere with nucleotide synthesis. Plant derivatives such a paclitaxel and vinblastine are mitotic spindle poisons. The podophyllotoxins inhibit topoisomerases, thus interfering with DNA replication. Antibiotics doxorubicin, bleomycin, and mitomycin interfere with DNA synthesis by intercalating between the bases of DNA (inhibiting uncoiling), causing strand breakage, and alkylating DNA, respectively. Other mechanisms of action include carbamoylation of amino acids (lomustine, carmustine), and depletion of asparagine pools (asparaginase). Merck Manual of Diagnosis and Therapy, 17$^{th}$ Edition, Section 11, Hematology and Oncology, 144. Principles of Cancer Therapy, Table 144-2 (1999). Specifically included among chemotherapeutic agents are those that directly affect the same cellular processes that are directly affected by the chemotherapeutic agents listed above.

A drug or treatment is "concurrently" administered with a Bi-Fc if it is administered in the same general time frame as the Bi-Fc, optionally, on an ongoing basis. For example, if a patient is taking Drug A once a week on an ongoing basis and a Bi-Fc once every six months on an ongoing basis, Drug A and the Bi-Fc are concurrently administered, whether or not they are ever administered on the same day. Similarly, if the Bi-Fc is taken once per week on an ongoing basis and Drug A is administered only once or a few times on a daily basis, Drug A and the Bi-Fc are concurrently administered as meant herein. Similarly, if both Drug A and the Bi-Fc are administered for short periods of time either once or multiple times within a one month period, they are administered concurrently as meant herein as long as both drugs are administered within the same month.

A "conservative amino acid substitution," as meant herein, is a substitution of an amino acid with another amino acid with similar properties. Properties considered include chemical properties such as charge and hydrophobicity. Table 1 below lists substitutions for each amino acid that are considered to be conservative substitutions as meant herein.

TABLE 1

Conservative Amino Acid Substitutions

| Original Residue | Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

As meant herein, an "Fc region" is a dimer consisting of two polypeptide chains joined by one or more disulfide bonds, each chain comprising part or all of a hinge domain plus a CH2 and a CH3 domain. Each of the polypeptide chains is referred to as an "Fc polypeptide chain." To distinguish the two Fc polypeptide chains, in some instances one is referred to herein as an "A chain" and the other is referred to as a "B chain." More specifically, the Fc regions contemplated for use with the present invention are IgG Fc regions, which can be mammalian, for example human, IgG1, IgG2, IgG3, or IgG4 Fc regions. Among human IgG1 Fc regions, at least two allelic types are known. In other embodiments, the amino acid sequences of the two Fc polypeptide chains can vary from those of a mammalian Fc polypeptide by no more than 10 amino acid substitutions, insertions, and/or deletions of a single amino acid per 100 amino acids relative to the sequence of a mammalian Fc polypeptide amino acid sequence. In some embodiments, such variations can be "heterodimerizing alterations" that facilitate the formation of heterodimers over homodimers, an Fc alteration that extends half life, an alteration that inhibits Fc gamma receptor (FcγR) binding, and/or an alteration that enhances ADCC.

An "Fc alteration that extends half life," as meant herein is an alteration within an Fc polypeptide chain that lengthens the in vivo half life of a protein that contains the altered Fc polypeptide chain as compared to the half life of a similar protein containing the same Fc polypeptide, except that it does not contain the alteration. Such alterations can be included in an Fc polypeptide chain that is part of a Bi-Fc. The alterations M252Y, S254T, and T256E (methionine at position 252 changed to tyrosine; serine at position 254 changed to threonine; and threonine at position 256 changed to glutamic acid; numbering according to EU numbering as shown in Table 2) are Fc alterations that extend half life and can be used together, separately or in any combination. These alterations and a number of others are described in detail in U.S. Pat. No. 7,083,784. The portions of U.S. Pat. No. 7,083,784 that describe such alterations are incorporated herein by reference. Similarly, M428L and N434S are Fc alterations that extend half life and can be used together, separately or in any combination. These alterations and a number of others are described in detail in U.S. Patent Application Publication 2010/0234575 and U.S. Pat. No. 7,670,600. The portions of U.S. Patent Application Publication 2010/0234575 and U.S. Pat. No. 7,670,600 that describe such alterations are incorporated herein by reference. In addition, any substitution at one of the following sites can be considered an Fc alteration that extends half life as meant here: 250, 251, 252, 259, 307, 308, 332, 378, 380, 428, 430, 434, 436. Each of these alterations or combinations of these alterations can be used to extend the half life of a heterodimeric bispecific antibody as described herein. Other alterations that can be used to extend half life are described in detail in International Application PCT/US2012/070146 filed Dec. 17, 2012. The portions of this application that describe such alterations are incorporated herein by reference. Some specific embodiments described in this application include insertions between positions 384 and 385 (EU numbering as shown in Table 2) that extend half life, including the following amino acid sequences: GGCVFNMFNCGG (SEQ ID NO:33), GGCHLPFAVCGG (SEQ ID NO:34), GGCGHEYMWCGG (SEQ ID NO:35), GGCWPLQDYCGG (SEQ ID NO:36), GGCMQMNKWCGG (SEQ ID NO:37), GGCDGRTKYCGG (SEQ ID NO:38), GGCALYPTNCGG (SEQ ID NO:39), GGCGKHWHQCGG (SEQ ID NO:40), GGCHSFKHFCGG (SEQ ID NO:41), GGCQGMWTWCGG (SEQ ID NO:42), GGCAQQWHHEYCGG (SEQ ID NO:43), and GGCERFHHACGG (SEQ ID NO:44), among others. Heterodimeric bispecific antibodies containing such insertions are contemplated.

An "Fc alteration that is unfavorable to homodimer formation," includes any alteration in an Fc polypeptide chain such that the Fc polypeptide chain has decreased ability to form homodimers compared to a wild type Fc polypeptide chain. Such alterations are described in detail in U.S. Patent Application Publication US2012/0244578. The portions of this publication that described such alteration are incorporated herein by reference. Such alterations can be included in an Fc polypeptide chain that is part of a Bi-Fc, especially in embodiments where the Bi-Fc is a monomer. In some embodiments, such alterations occur in the CH3 region of the Fc polypeptide chain and comprise an alteration such that one or more charged amino acids in the wild type amino acid sequence are replaced with amino acids electrostatically unfavorable to CH3 homodimer formation, and/or one or more hydrophobic interface residues are replaced with a small polar amino acid, such as, for example, asparagine, cysteine, glutamine, serine, or threonine. More specifically, for example, a charged amino acid, e.g., lysine at position 392 and/or position 409, can be replaced with a neutral or oppositely charged amino acid, for example aspartate or glutamate. This can also occur at any other charged amino acid within the Fc polypeptide chain. Alternatively or in addition, one or more hydrophobic interface residues selected from the group consisting of Y349, L351, L368, V397, L398, F405, and Y407 can be replaced with a small polar amino acid. Further, the Fc polypeptide chain can have one or more mutated cysteine residues to prevent di-sulfide bond formation. Particularly useful cysteine mutations in this regard are those in the hinge region of the Fc polypeptide chain. Such cysteines can be deleted or substituted with other amino acids.

"Heterodimerizing alterations" generally refer to alterations in the A and B chains of an Fc region that facilitate the formation of heterodimeric Fc regions, that is, Fc regions in which the A chain and the B chain of the Fc region do not have identical amino acid sequences. Such alterations can be included in an Fc polypeptide chain that is part of a Bi-Fc. Heterodimerizing alterations can be asymmetric, that is, an A chain having a certain alteration can pair with a B chain having a different alteration. These alterations facilitate heterodimerization and disfavor homodimerization. Whether hetero- or homo-dimers have formed can be assessed by size differences as determined by polyacrylamide gel electrophoresis in some situations or by other appropriate means (such as molecular tags or binding by antibodies that recognize certain portions of the heterodimer) in situations where size is not a distinguishing characteristic. One example of such paired heterodimerizing alterations are the so-called "knobs and holes" substitutions. See, e.g., U.S. Pat. No. 7,695,936 and US Patent Application Publication 2003/0078385, the portions of which describe such mutations are incorporated herein by reference. As meant herein, an Fc region that contains one pair of knobs and holes substitutions, contains one substitution in the A chain and another in the B chain. For example, the following knobs and holes substitutions in the A and B chains of an IgG1 Fc region have been found to increase heterodimer formation as compared with that found with unmodified A and B chains: 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; and 9) T366W in one polypeptide of the Fc and T366S, L368A, and Y407V in the other. This way of notating mutations can be explained as follows. The amino acid (using the one letter code) normally present at a given position in the CH3 region using the EU numbering system (which is presented in Edelman et al. (1969), Proc. Natl. Acad. Sci. 63: 78-85; see also Table 2 below) is followed by the EU position, which is followed by the alternate amino acid that is present at that position. For example, Y407T means that the tyrosine normally present at EU position 407 is replaced by a threonine. Alternatively or in addition to such alterations, substitutions creating new disulfide bridges can facilitate heterodimer formation. See, e.g., US Patent Application Publication 2003/0078385, the portions of which describe such mutations are incorporated herein by reference. Such alterations in an IgG1 Fc region include, for example, the following substitutions: Y349C in one Fc polypeptide chain and S354C in the other; Y349C in one Fc polypeptide chain and E356C in the other; Y349C in one Fc polypeptide chain and E357C in the other; L351C in one Fc polypeptide chain and S354C in the other; T394C in one Fc polypeptide chain and E397C in the other; or D399C in one Fc polypeptide chain and K392C in the other. Similarly, substitutions changing the charge of a one or more residue, for example, in the $C_H3$-$C_H3$ interface, can enhance heterodimer formation as explained in WO 2009/089004, the portions of which describe such substitutions are incorporated herein by reference. Such substitutions are referred to herein as "charge pair substitutions," and an Fc region containing one pair of charge pair substitutions contains one substitution in the A chain and a different substitution in the B chain. General examples of charge pair substitutions include the following: 1) K409D or K409E in one chain plus D399K or D399R in the other; 2) K392D or K392E in one chain plus D399K or D399R in the other; 3) K439D or K439E in one chain plus E356K or E356R in the other; and 4) K370D or K370E in one chain plus E357K or E357R in the other. In addition, the substitutions R355D, R355E, K360D, or K360R in both chains can stabilize heterodimers when used with other heterodimerizing alterations. Specific charge pair substitutions can be used either alone or with other charge pair substitutions. Specific examples of single pairs of charge pair substitutions and combinations thereof include the following: 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; and 17) K409D and K439D on one chain plus D399K and E356K on the other. Any of the these heterodimerizing alterations can be used in the Fc regions of the heterodimeric bispecific antibodies described herein.

An "alteration that inhibits FcγR binding," as meant herein, is one or more insertions, deletions, or substitutions within an Fc polypeptide chain that inhibits the binding of FcγRIIA, FcγRIIB, and/or FcγRIIIA as measured, for example, by an ALPHALISA®-based competition binding assay (Perkin Elmer, Waltham, Mass.). Such alterations can be included in an Fc polypeptide chain that is part of a Bi-Fc. More specifically, alterations that inhibit Fc gamma receptor (FcγR) binding include L234A, L235A, or any alteration that inhibits glycosylation at N297, including any substitution at N297. In addition, along with alterations that inhibit glycosylation at N297, additional alterations that stabilize a dimeric Fc region by creating additional disulfide bridges are also contemplated. Further examples of alterations that inhibit FcγR binding include a D265A alteration in one Fc polypeptide chain and an A327Q alteration in the other Fc polypeptide chain. Some such mutations are described in, e.g., Xu et al. (2000), Cellular Immunol. 200: 16-26, the portions of which describe such mutations and how their activity is assessed are incorporated herein by reference.

An "alteration that enhances ADCC," as meant herein is one or more insertions, deletions, or substitutions within an Fc polypeptide chain that enhances antibody dependent cell-mediated cytotoxicity (ADCC). Such alterations can be included in an Fc polypeptide chain that is part of a Bi-Fc. Many such alterations are described in International Patent Application Publication WO 2012/125850. Portions of this application that describe such alterations are incorporated herein by reference. Such alterations can be included in an Fc polypeptide chain that is part of a heterodimeric bispecific antibody as described herein. ADCC assays can be performed as follows. Cell lines that express high and lower amounts of a cancer cell antigen on the cell surface can be used as target cells. These target cells can be labeled with carboxyfluorescein succinimidyl ester (CFSE) and then washed once with phosphate buffered saline (PBS) before being deposited into 96-well microtiter plates with V-shaped wells. Purified immune effector cells, for example T cells, NK cells, macrophages, neutrophils can be added to each well. A monospecific antibody that binds to the cancer antigen and contains the alteration(s) being tested and an isotype-matched control antibody can be diluted in a 1:3 series and added to the wells. The cells can be incubated at 37° C. with 5% $CO_2$ for 3.5 hrs. The cells can be spun down and re-suspended in 1×FACS buffer (lx phosphate buffered saline (PBS) containing 0.5% fetal bovine serum (FBS)) with the dye TO-PRO®-3 iodide (Molecular Probes, Inc. Corporation, Oregon, USA), which stains dead cells, before analysis by fluorescence activated cell sorting (FACS). The percentage of cell killing can be calculated using the follow formula:

(percent tumor cell lysis with bispecific–percent tumor cell lysis without bispecific)/(percent total cell lysis–percent tumor cell lysis without bispecific)

Total cell lysis is determined by lysing samples containing effector cells and labeled target cells without a bispecific molecule with cold 80% methanol. Exemplary alterations that enhance ADCC include the following alterations in the A and B chains of an Fc region: (a) the A chain comprises Q311M and K334V substitutions and the B chain comprises L234Y, E294L, and Y296W substitutions or vice versa; (b) the A chain comprises E233L, Q311M, and K334V substitutions and the B chain comprises L234Y, E294L, and Y296W substitutions or vice versa; (c) the A chain comprises L234I, Q311M, and K334V substitutions and the B chain comprises L234Y, E294L, and Y296W substitutions or vice versa; (d) the A chain comprises S298T and K334V substitutions and the B chain comprises L234Y, K290Y, and Y296W substitutions or vice versa; (e) the A chain comprises A330M and K334V substitutions and the B chain comprises L234Y, K290Y, and Y296W substitutions or vice versa; (f) the A chain comprises A330F and K334V substitutions and the B chain comprises L234Y, K290Y, and Y296W substitutions or vice versa; (g) the A chain comprises Q311M, A330M, and K334V substitutions and the B chain comprises L234Y, E294L, and Y296W substitutions or vice versa; (h) the A chain comprises Q311M, A330F, and K334V substitutions and the B chain comprises L234Y, E294L, and Y296W substitutions or vice versa; (i) the A chain comprises S298T, A330M, and K334V substitutions and the B chain comprises L234Y, K290Y, and Y296W substitutions or vice versa; (j) the A chain comprises S298T, A330F, and K334V substitutions and the B chain comprises L234Y, K290Y, and Y296W substitutions or vice versa; (k) the A chain comprises S239D, A330M, and K334V substitutions and the B chain comprises L234Y, K290Y, and Y296W substitutions or vice versa; (l) the A chain comprises S239D, S298T, and K334V substitutions and the B chain comprises L234Y, K290Y, and Y296W substitutions or vice versa; (m) the A chain comprises a K334V substitution and the B chain comprises Y296W and S298C substitutions or vice versa; (n) the A chain comprises a K334V substitution and the B chain comprises L234Y, Y296W, and S298C substitutions or vice versa; (o) the A chain comprises L235S, S239D, and K334V substitutions and the B chain comprises L234Y, K290Y, and Y296W, substitutions or vice versa; (p) the A chain comprises L235S, S239D, and K334V substitutions and the B chain comprises L234Y, Y296W, and S298C substitutions or vice versa; (q) the A chain comprises Q311M and K334V substitutions and the B chain comprises L234Y, F243V, and Y296W substitutions or vice versa; (r) the A chain comprises Q311M and K334V substitutions and the B chain comprises L234Y, K296W, and S298C substitutions or vice versa; (s) the A chain comprises S239D and K334V substitutions and the B chain comprises L234Y, K290Y, and Y296W substitutions or vice versa; (t) the A chain comprises S239D and K334V substitutions and the B chain comprises L234Y, Y296W, and S298C substitutions or vice versa; (u) the A chain comprises F243V and K334V substitutions and the B chain comprises L234Y, K290Y, and Y296W, substitutions or vice versa; (v) the A chain comprises F243V and K334V substitutions and the B chain comprises L234Y, Y296W, and S298C substitutions or vice versa; (w) the A chain comprises E294L and K334V substitutions and the B chain comprises L234Y, K290Y, and Y296W substitutions or vice versa; (x) the A chain comprises E294L and K334V substitutions and the B chain comprises L234Y, Y296W, and S298C substitutions or vice versa; (y) the A chain comprises A330M and K334V substitutions and the B chain comprises L234Y and Y296W substitutions or vice versa; or (z) the A chain comprises A330M and K334V substitutions and the B chain comprises K290Y and Y296W substitutions or vice versa.

An "IgG antibody," as meant herein, is an antibody consisting essentially of two immunoglobulin IgG heavy chains and two immunoglobulin light chains, which can be kappa or lambda light chains. More specifically, the heavy chains contain a VH region, a CH1 region, a hinge region, a CH2 region, and a CH3 region in that order, while the light chains contain a VL region followed by a CL region. Numerous sequences of such immunoglobulin regions are known in the art. See, e.g., Kabat et al. in SEQUENCES OF IMMUNOLOGICAL INTEREST, Public Health Service N.I.H., Bethesda, Md., 1991. Sequences of regions from IgG antibodies disclosed in Kabat et al. are incorporated herein by reference. Close variants of a known and/or naturally-occurring IgG antibody comprising no more than 10 amino acid substitutions, insertions, and/or deletions of a single amino acid per 100 amino acids relative to a known or naturally occurring sequence of an immunoglobulin IgG heavy and/or light chain are encompassed within what is meant by an IgG antibody.

An "immune effector cell," as meant herein, is a cell that is involved in the mediation of a cytolytic immune response, including, for example, T cells, NK cells, macrophages, or neutrophils. The heterodimeric bispecific antibodies described herein bind to an antigen that is part of a protein expressed on the surface of an immune effector cell. Such proteins are referred to herein as "effector cell proteins."

An "immunoglobulin heavy chain," as meant herein, consists essentially of a VH region, a CH1 region, a hinge region, a CH2 region, a CH3 region in that order, and, optionally, a region downstream of the CH3 region in some isotypes. Close variants of an immunoglobulin heavy chain containing no more than 10 amino acid substitutions, insertions, and/or deletions of a single amino acid per 100 amino acids relative to a known or naturally occurring immunoglobulin heavy chain amino acid sequence are encompassed within what is meant by an immunoglobulin heavy chain.

A "immunoglobulin light chain," as meant herein, consists essentially of a light chain variable region (VL) and a light chain constant domain (CL). Close variants of an immunoglobulin light chain containing no more than 10 amino acid substitutions, insertions, and/or deletions of a single amino acid per 100 amino acids relative to a known or naturally occurring immunoglobulin light chain amino acid sequence are encompassed within what is meant by an immunoglobulin light chain.

An "immunoglobulin variable region," as meant herein, is a VH region, a VL region, or a variant thereof. Close variants of an immunoglobulin variable region containing no more than 10 amino acid substitutions, insertions, and/or deletions of a single amino acid per 100 amino acids relative to a known or naturally occurring immunoglobulin variable region amino acid sequence are encompassed within what is meant by an immunoglobulin variable region. Many examples of VH and VL regions are known in the art, such as, for example, those disclosed by Kabat et al. in SEQUENCES OF IMMUNOLOGICAL INTEREST, Public Health Service N.I.H., Bethesda, Md., 1991. Based on the extensive sequence commonalities in the less variable portions of the VH and VL regions, the position within a sequence of more variable regions, and the predicted tertiary structure, one of skill in the art can recognize an immunoglobulin variable region by its sequence. See, e.g., Honegger and Plückthun (2001), J. Mol. Biol. 309: 657-670.

An immunoglobulin variable region contains three hypervariable regions, known as complementarity determining region 1 (CDR1), complementarity determining region 2 (CDR2), and complementarity determining region 3 (CDR3). These regions form the antigen binding site of an antibody. The CDRs are embedded within the less variable framework regions (FR1-FR4). The order of these subregions within an immunoglobulin variable region is as follows: FR1-CDR1-FR2-CDR2-FR3-CDR3-FR4. Numerous sequences of immunoglobulin variable regions are known in the art. See, e.g., Kabat et al., SEQUENCES OF PROTEINS OF IMMUNOLOGICAL INTEREST, Public Health Service N.I.H., Bethesda, Md., 1991.

CDRs can be located in a VH region sequence in the following way. CDR1 starts at approximately residue 31 of the mature VH region and is usually about 5-7 amino acids long, and it is almost always preceded by a Cys-Xxx-Xxx-Xxx-Xxx-Xxx-Xxx-Xxx-Xxx (SEQ ID NO:1) (where "Xxx" is any amino acid). The residue following the heavy chain CDR1 is almost always a tryptophan, often a Trp-Val, a Trp-Ile, or a Trp-Ala. Fourteen amino acids are almost always between the last residue in CDR1 and the first in CDR2, and CDR2 typically contains 16 to 19 amino acids. CDR2 may be immediately preceded by Leu-Glu-Trp-Ile-Gly (SEQ ID NO:2) and may be immediately followed by Lys/Arg-Leu/Ile/Val/Phe/Thr/Ala-Thr/Ser/Ile/Ala. Other amino acids may precede or follow CDR2. Thirty two amino acids are almost always between the last residue in CDR2 and the first in CDR3, and CDR3 can be from about 3 to 25 residues long. A Cys-Xxx-Xxx almost always immediately precedes CDR3, and a Trp-Gly-Xxx-Gly (SEQ ID NO:3) almost always follows CDR3.

Light chain CDRs can be located in a VL region in the following way. CDR1 starts at approximately residue 24 of the mature antibody and is usually about 10 to 17 residues long. It is almost always preceded by a Cys. There are almost always 15 amino acids between the last residue of CDR1 and the first residue of CDR2, and CDR2 is almost always 7 residues long. CDR2 is typically preceded by Ile-Tyr, Val-Tyr, Ile-Lys, or Ile-Phe. There are almost always 32 residues between CDR2 and CDR3, and CDR3 is usually about 7 to 10 amino acids long. CDR3 is almost always preceded by Cys and usually followed by Phe-Gly-Xxx-Gly (SEQ ID NO:4).

A "linker," as meant herein, is a peptide that links two polypeptides, which can be two immunoglobulin variable regions in the context of a heterodimeric bispecific antibody. A linker can be from 2-30 amino acids in length. In some embodiments, a linker can be 2-25, 2-20, or 3-18 amino acids long. In some embodiments, a linker can be a peptide no more than 14, 13, 12, 11, 10, 9, 8, 7, 6, or 5 amino acids long. In other embodiments, a linker can be 5-25, 5-15, 4-11, 10-20, or 20-30 amino acids long. In other embodiments, a linker can be about, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids long. Exemplary linkers include, for example, the amino acid sequences TVAAP (SEQ ID NO:17), ASTKGP (SEQ ID NO:18), GGGGSGGGGS (SEQ ID NO:19), GGGGSAAA (SEQ ID NO:20), GGGGSGGGGSGGGGS (SEQ ID NO:21), and AAA, among many others.

A Bi-Fc "mediates cytolysis of a target cell by an immune effector cell," as meant herein, when addition of an amount from 0.001 pM to 20000 pM of the Bi-Fc to a cell cytolysis assay as described in the section below entitled "Target Cell Cytolysis Assays" and in Example 3 effectively elicits cytolysis of the target cells.

"Non-chemotherapeutic anti-neoplastic agents" are chemical agents, compounds, or molecules having cytotoxic or cytostatic effects on cancer cells other than chemotherapeutic agents. Non-chemotherapeutic antineoplastic agents may, however, be targeted to interact directly with molecules that indirectly affect cell division such as cell surface receptors, including receptors for hormones or growth factors. However, non-chemotherapeutic antineoplastic agents do not interfere directly with processes that are intimately linked to cell division such as, for example, DNA replication, RNA synthesis, protein synthesis, or mitotic spindle function, assembly, or disassembly. Examples of non-chemotherapeutic anti-neoplastic agents include inhibitors of Bcl2, inhibitors of farnesyltransferase, anti-estrogenic agents such as tamoxifen, anti-androgenic compounds, interferon, arsenic, retinoic acid, retinoic acid derivatives, antibodies targeted to tumor-specific antigens, and inhibitors of the Bcr-Abl tyrosine kinase (e.g., the small molecule STI-571 marketed under the trade name GLEEVEC™ by Novartis, New York and New Jersey, USA and Basel, Switzerland), among many possible non-chemotherapeutic antineoplastic agents.

A "target cell" is a cell that a Bi-Fc binds to and that is involved in mediating a disease. In some cases, a target cell can be a cell that is ordinarily involved in mediating an immune response, but is also involved in the mediation of a disease. For example in B cell lymphoma, a B cell, which is ordinarily involved in mediating immune response, can be a target cell. In some embodiments, a target cell is a cancer cell, a cell infected with a pathogen, or a cell involved in mediating an autoimmune or inflammatory disease, for example a fibrotic disease. The Bi-Fc can bind to the target cell via binding to an antigen on a "target cell protein," which is a protein that is displayed on the surface of the target cell, possibly a highly expressed protein.

"Tumor burden" refers to the number of viable cancer cells, the number of tumor sites, and/or the size of the tumor(s) in a patient suffering from a cancer. A reduction in tumor burden can be observed, for example, as a reduction in the amount of a tumor-associated antigen or protein in a patient's blood or urine, a reduction in the number of tumor cells or tumor sites, and/or a reduction in the size of one or more tumors.

A "therapeutically effective amount" of a Bi-Fc or any other drug is an amount that has the effect of, for example, reducing or eliminating the tumor burden of a cancer patient or reducing or eliminating the symptoms of any disease condition that the protein is used to treat. A therapeutically effective amount need not completely eliminate all symptoms of the condition, but may reduce severity of one or more symptoms or delay the onset of more serious symptoms or a more serious disease that can occur with some frequency following the treated condition.

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition.

When it is said that a named VH/VL pair of immunoglobulin variable regions can bind to a target cell or and/or an immune effector cell "when they are part of an IgG and/or scFv antibody," it is meant that an IgG antibody that contains the named VH region in both heavy chains and the named VL region in both light chains and/or an scFv antibody containing these VH and VL regions can bind to the target cell and/or the immune effector cell. The binding assay described in Example 2 can be used to assess binding.

Bi-Fc Molecules

In the most general sense, a Bi-Fc can bind monovalently to two different antigens and comprises one polypeptide chain or two different polypeptide chains having different amino acid sequences. In addition, it can bind to the neonatal Fc receptor (FcRn) at slightly acidic pH (about pH 5.5-6.0) via its Fc region. This interaction with FcRn can lenthen the half life of a molecule in vivo. The first polypeptide chain (which, in some cases, is the only polypeptide chain) comprises an Fc polypeptide chain and two VH regions plus two VL regions separated by linkers. The Fc polypeptide chain can be N-terminal or C-terminal relative to the four immunoglobulin variable regions, and it can be joined to the variable regions via a linker. The second polypeptide chain, when present, comprises an Fc polypeptide chain. A Bi-Fc can bind to an immune effector cell and a target cell and/or can mediate cytolysis of a target cell by an immune effector cell. The general structure of a Bi-Fc is diagrammed in FIG. 1, which shows an embodiment where the Fc polypeptide chain is C-terminal (at left) and an embodiment where the Fc polypeptide chain in N-terminal (at right).

More particular embodiments specify the order of immunoglobulin variable regions and the length of the linkers and specify which immunoglobulin variable regions can associate to form a binding site for an effector cell protein or a target cell protein. Generally, the antigen-binding portion of an antibody includes both a VH and a VL region, referred to herein as a "VH/VL pair," although in some cases a VH or a VL region can bind to an antigen without a partner. See, e.g., US Application Publication 2003/0114659.

In one group of embodiments, the four variable regions can be arranged in the following order: VH1-linker1-VL1-linker2-VH2-linker3-VL2, where VH1/VL1 is an antigen-binding pair and VH2/VL2 is another antigen-binding pair. In this group of embodiments, linker1 and linker3 can be at least 15 amino acids long, and linker2 can be less than 12 amino acids long. In some embodiments, the VH1/VL1 pair can bind to a target cell protein, and the VH2/VL2 pair can bind to an effector cell protein. In other embodiments, the VH1/VL1 pair can bind to an effector cell protein, and the VH2/VL2 pair can bind to a target cell protein.

In another group of embodiments the four variable regions can be arranged in the following order: VL1-linker1-VH1-linker2-VL2-linker3-VH2, where VH1/VL1 is an antigen-binding pair and VH2/VL2 is an antigen-binding pair. In these embodiments, linker2 can be less than 12 amino acids long, and linker1 and linker3 can be at least 15 amino acids long. In some embodiments, the VH1/VL1 pair can bind to a target cell protein, and the VH2/VL2 pair can bind to an effector cell protein. In other embodiments, the VH1/VL1 pair can bind to an effector cell protein, and the VH2/VL2 pair can bind to a target cell protein.

In another group of embodiments the four variable regions can be arranged in the following order: VH1-linker1-VL1-linker2-VL2-linker3-VH2, where VH1/VL1 is an antigen-binding pair and VH2/VL2 is an antigen-binding pair. In these embodiments, linker2 can be less than 12 amino acids long, and linker1 and linker3 can be at least 15 amino acids long. In some embodiments, the VH1/VL1 pair can bind to a target cell protein, and the VH2/VL2 pair can bind to an effector cell protein. In other embodiments, the VH1/VL1 pair can bind to an effector cell protein, and the VH2/VL2 pair can bind to a target cell protein.

In further group of embodiments the four variable regions can be arranged in the following order: VL1-linker1-VH1-linker2-VH2-linker3-VL2, where VH1/VL1 is an antigen-binding pair and VH2/VL2 is an antigen-binding pair. In these embodiments, linker2 can be less than 12 amino acids long, and linked and linker3 can be at least 15 amino acids long. In some embodiments, the VH1/VL1 pair can bind to a target cell protein, and the VH2/VL2 pair can bind to an effector cell protein. In other embodiments, the VH1/VL1 pair can bind to an effector cell protein, and the VH2/VL2 pair can bind to a target cell protein.

A Bi-Fc can comprise an Fc polypeptide chain of an antibody. The Fc polypeptide chain can be of mammalian (for example, human, mouse, rat, rabbit, dromedary, or new or old world monkey), avian, or shark origin. For example, the Fc polypeptide chain can be a human IgG1, IgG2, IgG3, or IgG4 Fc polypeptide chain. In addition, as explained above, an Fc polypeptide chain can comprise a limited number of alterations. More particularly, an Fc polypeptide chain can contain no more than 10 insertions, deletions, and/or substitutions of a single amino acid per 100 amino acids relative to a known or naturally-occurring sequence. In some embodiments, the two Fc polypeptide chains of a heterodimeric Bi-Fc contain heterodimerizing alterations, In some embodiments the amino acid sequences of the Fc polypeptides can be mammalian, for example a human, amino acid sequences or variants thereof that comprise not more than 10 deletions, insertions, or substitutions of a single amino acid per 100 amino acids of sequence relative to a human amino acid sequence. The isotype of the Fc polypeptide can be IgA, IgD, IgE, IgM, or IgG, such as IgG1, IgG2, IgG3, or IgG4. Table 2 below shows an alignment of the amino acid sequences of human IgG1, IgG2, IgG3, and IgG4 Fc polypeptide chain sequences.

TABLE 2

Amino acid sequences of human IgG Fc regions

```
IgG1   ------------------------------------------------
IgG2   ------------------------------------------------
IgG3   ELKTPLGDTTHTCPRCPEPKSCDTPPPCPRCPEPKSCDTPPPCPRCP
IgG4   ------------------------------------------------

225       235       245       255       265       275
          *         *         *         *         *         *
IgG1   EPKSCDKTHTCPPCPAPELLGGPSVFLFPPKPKDTLMISRTPEVTCVVVDVSHEDPEVKF
IgG2   ERKCCVE---CPPCPAPPVA-GPSVFLFPPKPKDTLMISRTPEVTCVVVDVSHEDPEVQF
IgG3   EPKSCDTPPPCPRCPAPELLGGPSVFLFPPKPKDTLMISRTPEVTCVVVDVSHEDPEVQF
IgG4   ESKYG---PPCPSCPAPEFLGGPSVFLFPPKPKDTLMISRTPEVTCVVVDVSQEDPEVQF 285       295       305       315       325       335
          *         *         *         *         *         *
IgG1   NWYVDGVEVHNAKTKPREEQYNSTYRVVSVLTVLHQDWLNGKEYKCKVSNKALPAPIEKT
IgG2   NWYVDGMEVHNAKTKPREEQFNSTFRVVSVLTVVHQDWLNGKEYKCKVSNKGLPAPIEKT
IgG3   KWYVDGVEVHNAKTKPREEQYNSTFRVVSVLTVLHQDWLNGKEYKCKVSNKALPAPIEKT
IgG4   NWYVDGVEVHNAKTKPREEQFNSTYRVVSVLTVLHQDWLNGKEYKCKVSNKGLPSSIEKT 345       355       365       375       385       395
          *         *         *         *         *         *
IgG1   ISKAKGQPREPQVYTLPPSRDELTKNQVSLTCLVKGFYPSDIAVEWESNGQPENNYKTTP
IgG2   ISKTKGQPREPQVYTLPPSREEMTKNQVSLTCLVKGFYPSDIAVEWESNGQPENNYKTTP
IgG3   ISKTKGQPREPQVYTLPPSREEMTKNQVSLTCLVKGFYPSDIAVEWESSGQPENNYNTTP
IgG4   ISKAKGQPREPQVYTLPPSQEEMTKNQVSLTCLVKGFYPSDIAVEWESNGQPENNYKTTP 405       415       425       435       445
          *         *         *         *         *         *
IgG1   PVLDSDGSFFLYSKLTVDKSRWQQGNVFSCSVMHEALHNHYTQKSLSLSPGK (SEQ ID NO: 25)
IgG2   PMLDSDGSFFLYSKLTVDKSRWQQGNVFSCSVMHEALHNHYTQKSLSLSPGK (SEQ ID NO: 26)
IgG3   PMLDSDGSFFLYSKLTVDKSRWQQGNIFSCSVMHEALHNRFTQKSLSLSPGK (SEQ ID NO: 27)
IgG4   PVLDSDGSFFLYSRLTVDKSRWQEGNVFSCSVMHEALHNHYTQKSLSLSLGK (SEQ ID NO: 28)
``` which can be, for example, charge pair substitutions. For example, the first polypeptide chain of the Bi-Fc can comprise the substitutions K409D or K409E and K392D or K392E and the second polypeptide chain of the Bi-Fc can comprise D399K or D399R and D356K or D356R. Alternatively, the first polypeptide chain of the Bi-Fc can comprise D399K or D399R and D356K or D356R, and the second polypeptide chain of the Bi-Fc can comprise K409D or K409E and K392D or K392E. An Fc polypeptide chain can also comprise one or more "Fc alterations unfavorable to homodimer formation" and/or one or more "Fc alterations that extend half life," as meant herein.

In monomeric embodiments of the Bi-Fc, the Bi-Fc can comprise one or more "Fc alterations that are unfavorable to homodimer formation," as defined above.

Other kinds of alteration can also be part of an Fc polypeptide chain that is part of a Bi-Fc. In one aspect, an Fc region included in a Bi-Fc can comprise one or more "alterations that inhibit the binding of an Fc gamma receptor (FcγR)" to the Fc region as defined above. In another aspect, an Fc region included in a Bi-Fc can comprise one or more "Fc alterations that extends half life," as defined above. In still another aspect, one or more "alterations that enhance ADCC" can be included in an Fc region that is part of a Bi-Fc.

The numbering shown in Table 2 is according the EU system of numbering, which is based on the sequential numbering of the constant region of a human IgG1 antibody. Edelman et al. (1969), Proc. Natl. Acad. Sci. 63: 78-85. Thus, it does not accommodate the additional length of the IgG3 hinge well. It is nonetheless used herein to designate positions in an Fc region because it is still commonly used in the art to refer to positions in Fc regions. The hinge regions of the IgG1, IgG2, and IgG4 Fc polypeptides extend from about position 216 to about 230. It is clear from the alignment that the IgG2 and IgG4 hinge regions are each three amino acids shorter than the IgG1 hinge. The IgG3 hinge is much longer, extending for an additional 47 amino acids upstream. The CH2 region extends from about position 231 to 340, and the CH3 region extends from about position 341 to 447.

Naturally occurring amino acid sequences of Fc polypeptides can be varied slightly. Such variations can include no more than 10 insertions, deletions, and/or substitutions of one amino acid per 100 amino acids of sequence in a known or naturally-occurring amino acid sequence of an Fc polypeptide. If there are substitutions, they can be conservative amino acid substitutions, as defined above. The Fc polypeptides on the first and second polypeptide chains of a Bi-Fc can differ in amino acid sequence. In some embodiments, they can include one or more "heterodimerizing alterations," "alterations that enhance ADCC," "alterations that inhibit FcγR binding," "Fc alterations that are unfavorable to homodimer formation," and/or "Fc alterations that extend half life," as defined above.

A Bi-Fc can bind to an immune effector cell through an antigen that is part of an effector cell protein and can bind to a target cell through an antigen that is part of a target cell protein. A number of possible effector cell proteins are described in detail below. Similarly, a number of possible target cell proteins is also described below. A Bi-Fc can bind to any combination of an effector cell protein and a target cell protein.

Exemplary amino acid sequences of Bi-Fc's include the following pairs of amino acid sequences: SEQ ID NOs:10 and 12 and SEQ ID NOs:15 and 12.

Nucleic Acids Encoding Bi-Fc Molecules

Provided are nucleic acids encoding Bi-Fc's. Numerous nucleic acid sequences encoding immunoglobulin regions including VH, VL, hinge, CH1, CH2, CH3, and CH4 regions are known in the art. See, e.g., Kabat et al. in SEQUENCES OF IMMUNOLOGICAL INTEREST, Public Health Service N.I.H., Bethesda, Md., 1991. Using the guidance provided herein, one of skill in the art could combine such nucleic acid sequences and/or other nucleic acid sequences known in the art to create nucleic acid sequences encoding Bi-Fc's. Exemplary pairs of nucleic acids encoding Bi-Fc's include SEQ ID NOs:11 and 13 and SEQ ID NOs:16 and 13.

In addition, nucleic acid sequences encoding Bi-Fc's can be determined by one of skill in the art based on the amino acid sequences provided herein and elsewhere and knowledge in the art. Besides more traditional methods of producing cloned DNA segments encoding a particular amino acid sequence, companies such as DNA 2.0 (Menlo Park, Calif., USA) and BlueHeron (Bothell, Wash., USA), among others, now routinely produce chemically synthesized, gene-sized DNAs of any desired sequence to order, thus streamlining the process of producing such DNAs.

Methods of Making Bi-Fc Molecules

Bi-Fc's can be made using methods well known in the art. For example, nucleic acids encoding the one or two polypeptide chains of a Bi-Fc can be introduced into a cultured host cell by a variety of known methods, such as, for example, transformation, transfection, electroporation, bombardment with nucleic acid-coated microprojectiles, etc. In some embodiments the nucleic acids encoding a Bi-Fc can be inserted into a vector appropriate for expression in the host cells before being introduced into the host cells. Typically such vectors can contain sequence elements enabling expression of the inserted nucleic acids at the RNA and protein levels. Such vectors are well known in the art, and many are commercially available. The host cells containing the nucleic acids can be cultured under conditions so as to enable the cells to express the nucleic acids, and the resulting Bi-Fc's can be collected from the cell mass or the culture medium. Alternatively, a Bi-Fc can be produced in vivo, for example in plant leaves (see, e.g., Scheller et al. (2001), Nature Biotechnol. 19: 573-577 and references cited therein), bird eggs (see, e.g., Zhu et al. (2005), Nature Biotechnol. 23: 1159-1169 and references cited therein), or mammalian milk (see, e.g., Laible et al. (2012), Reprod. Fertil. Dev. 25(1): 315).

A variety of cultured host cells can be used including, for example, bacterial cells such as *Escherichia coli* or *Bacillus stearothermophilus*, fungal cells such as *Saccharomyces cerevisiae* or *Pichia pastoris*, insect cells such as lepidopteran insect cells including *Spodoptera frugiperda* cells, or mammalian cells such as Chinese hamster ovary (CHO) cells, baby hamster kidney (BHK) cells, monkey kidney cells, HeLa cells, human hepatocellular carcinoma cells, or 293 cells, among many others.

Immune Effector Cells and Effector Cell Proteins

A Bi-Fc can bind to a molecule expressed on the surface of an immune effector cell (called "effector cell protein" herein) and to another molecule expressed on the surface of a target cell (called a "target cell protein" herein). The immune effector cell can be a T cell, an NK cell, a macrophage, or a neutrophil. In some embodiments the effector cell protein is a protein included in the T cell receptor (TCR)-CD3 complex. The TCR-CD3 complex is a heteromultimer comprising a heterodimer comprising TCRα and TCRβ or TCRγ and TCRδ plus various CD3 chains from among the CD3 zeta (CD3ζ) chain, CD3 epsilon (CD3ε) chain, CD3 gamma (CD3γ) chain, and CD3 delta (CD3δ) chain. In some embodiments the effector cell protein can be the human CD3 epsilon (CD3ε) chain (the mature amino acid sequence of which is disclosed in SEQ ID NO:22), which can be part of a multimeric protein. Alternatively, the effector cell protein can be human and/or cynomolgus monkey TCRα, TCRβ, TCRδ, TCRγ, CD3 beta (CD3β) chain, CD3 gamma (CD3γ) chain, CD3 delta (CD3δ) chain, or CD3 zeta (CD3ζ) chain.

Moreover, in some embodiments, a Bi-Fc can also bind to a CD3ε chain from a non-human species, such as mouse, rat, rabbit, new world monkey, and/or old world monkey species. Such species include, without limitation, the following mammalian species: *Mus musculus; Rattus rattus; Rattus norvegicus*; the cynomolgus monkey, *Macaca fascicularis*; the hamadryas baboon, *Papio hamadryas*; the Guinea baboon, *Papio papio*; the olive baboon, *Papio anubis*; the yellow baboon, *Papio cynocephalus*; the Chacma baboon, *Papio ursinus; Callithrix jacchus; Saguinus Oedipus*, and *Saimiri sciureus*. The mature amino acid sequence of the CD3ε chain of cynomolgus monkey is provided in SEQ ID NO:23. As is known in the art of development of protein therapeutics, having a therapeutic that can have comparable activity in humans and species commonly used for preclinical testing, such as mice and monkeys, can simplify and speed drug development. In the long and expensive process of bringing a drug to market, such advantages can be critical.

In more particular embodiments, the heterodimeric bispecific antibody can bind to an epitope within the first 27 amino acids of the CD3ε chain, which may be a human CD3ε chain or a CD3ε chain from different species, particularly one of the mammalian species listed above. The epitope can contain the amino acid sequence Gln-Asp-Gly-Asn-Glu (SEQ ID NO:24). The advantages of an antibody that binds such an epitope are explained in detail in U.S. Patent Application Publication 2010/183615, the relevant portions of which are incorporated herein by reference. The epitope to which an antibody binds can be determined by alanine scanning, which is described in, e.g., U.S. Patent Application Publication 2010/183615, the relevant portions of which are incorporated herein by reference.

Where a T cell is the immune effector cell, effector cell proteins to which a Bi-Fc can bind include, without limitation, the CD3ε chain, the CD3γ, the CD3δ chain, the CD3ζ chain, TCRα, TCRβ, TCRγ, and TCRδ. Where an NK cell or a cytotoxic T cell is an immune effector cell, NKG2D, CD352, NKp46, or CD16a can, for example, be an effector cell protein. Where a CD8+ T cell is an immune effector cell, 4-1BB or NKG2D, for example, can be an effector cell protein. Alternatively, a Bi-Fc could bind to other effector cell proteins expressed on T cells, NK cells, macrophages, or neutrophils.

Target Cells and Target Cell Proteins Expressed on Target Cells

As explained above, a Bi-Fc can bind to an effector cell protein and a target cell protein. The target cell protein can, for example, be expressed on the surface of a cancer cell, a cell infected with a pathogen, or a cell that mediates a disease, for example an inflammatory, autoimmune, and/or fibrotic condition. In some embodiments, the target cell protein can be highly expressed on the target cell, although high levels of expression are not necessarily required.

Where the target cell is a cancer cell, a heterodimeric bispecific antibody as described herein can bind to a cancer cell antigen as described above. A cancer cell antigen can be a human protein or a protein from another species. For example, a heterodimeric bispecific antibody may bind to a target cell protein from a mouse, rat, rabbit, new world monkey, and/or old world monkey species, among many others. Such species include, without limitation, the following species: *Mus musculus; Rattus rattus; Rattus norvegicus*; cynomolgus monkey, *Macaca fascicularis*; the hamadryas baboon, *Papio hamadryas*; the Guinea baboon, *Papio papio*; the olive baboon, *Papio anubis*; the yellow baboon, *Papio cynocephalus*; the Chacma baboon, *Papio ursinus, Callithrix jacchus, Saguinus oedipus*, and *Saimiri sciureus*.

In some examples, the target cell protein can be a protein selectively expressed on an infected cell. For example, in the case of an HBV or HCV infection, the target cell protein can be an envelope protein of HBV or HCV that is expressed on the surface of an infected cell. In other embodiments, the target cell protein can be gp120 encoded by human immunodeficiency virus (HIV) on HIV-infected cells.

In other aspects, a target cell can be a cell that mediates an autoimmune or inflammatory disease. For example, human eosinophils in asthma can be target cells, in which case, EGF-like module containing mucin-like hormone receptor (EMR1), for example, can be a target cell protein. Alternatively, excess human B cells in a systemic lupus erythematosus patient can be target cells, in which case CD19 or CD20, for example, can be a target cell protein. In other autoimmune conditions, excess human Th2 T cells can be target cells, in which case CCR4 can, for example, be a target cell protein. Similarly, a target cell can be a fibrotic cell that mediates a disease such as atherosclerosis, chronic obstructive pulmonary disease (COPD), cirrhosis, scleroderma, kidney transplant fibrosis, kidney allograft nephropathy, or a pulmonary fibrosis, including idiopathic pulmonary fibrosis and/or idiotypic pulmonary hypertension. For such fibrotic conditions, fibroblast activation protein alpha (FAP alpha) can, for example, be a target cell protein.

Target Cell Cytolysis Assays

In the Examples below, an assay for determining whether a heterodimeric bispecific antibody as described herein can induce cytolysis of a target cell by an immune effector cell in vitro is described. In this assay, the immune effector cell is a T cell. The following very similar assay can be used where the immune effector cells are NK cells.

A target cell line expressing the target cell protein of interest can be labeled with 2 μM carboxyfluorescein succinimidyl ester (CFSE) for 15 minutes at 37° C. and then washed. An appropriate number of labeled target cells can then be incubated in one or more 96 well flat bottom culture plates for 40 minutes at 4° C., with or without a bispecific protein, a control protein, or no added protein at varying concentrations. NK cells isolated from healthy human donors can be isolated using the Miltenyi NK Cell Isolation Kit II (Miltenyi Biotec, Auburn, Calif.) and then added to the target cells at an Effector:Target ratio of 10:1. The NK cells, which are the immune effector cells in this assay, can be used immediately post-isolation or after overnight culture at 37° C. Plates containing tumor target cells, bispecific proteins, and immune effector cells can be cultured for 18-24 hours at 37° C. with 5% CO2. Appropriate control wells can also be set up. After the 18-24 hour assay period, all cells can be removed from the wells. A volume of a 7-AAD solution equal to the volume of the content of the wells can be added to each sample. Samples can then assayed to determine the percentage of live versus dead target cells via flow cytometry as described in the Examples below.

Therapeutic Methods and Compositions

Bi-Fc's can be used to treat a wide variety of conditions including, for example, various forms of cancer, infections, autoimmune or inflammatory conditions, and/or fibrotic conditions.

Provided herein are pharmaceutical compositions comprising Bi-Fc's. Such pharmaceutical compositions comprise a therapeutically effective amount of a Bi-Fc plus one or more additional components such as a physiologically acceptable carrier, excipient, or diluent. Such additional components can include buffers, carbohydrates, polyols, amino acids, chelating agents, stabilizers, and/or preservatives, among many possibilities.

In some embodiments, a Bi-Fc can be used to treat cell proliferative diseases, including cancer, which involve the unregulated and/or inappropriate proliferation of cells, sometimes accompanied by destruction of adjacent tissue and growth of new blood vessels, which can allow invasion of cancer cells into new areas, i.e. metastasis. Included within conditions treatable with a Bi-Fc are non-malignant conditions that involve inappropriate cell growth, including colorectal polyps, cerebral ischemia, gross cystic disease, polycystic kidney disease, benign prostatic hyperplasia, and endometriosis. A Bi-Fc can be used to treat a hematologic or solid tumor malignancy. More specifically, cell proliferative diseases that can be treated using a Bi-Fc are, for example, cancers including mesotheliomas, squamous cell carcinomas, myelomas, osteosarcomas, glioblastomas, gliomas, carcinomas, adenocarcinomas, melanomas, sarcomas, acute and chronic leukemias, lymphomas, and meningiomas, Hodgkin's disease, Sézary syndrome, multiple myeloma, and lung, non-small cell lung, small cell lung, laryngeal, breast, head and neck, bladder, ovarian, skin, prostate, cervical, vaginal, gastric, renal cell, kidney, pancreatic, colorectal, endometrial, and esophageal, hepatobiliary, bone, skin, and hematologic cancers, as well as cancers of the nasal cavity and paranasal sinuses, the nasopharynx, the oral cavity, the oropharynx, the larynx, the hypolarynx, the salivary glands, the mediastinum, the stomach, the small intestine, the colon, the rectum and anal region, the ureter, the urethra, the penis, the testis, the vulva, the endocrine system, the central nervous system, and plasma cells.

Among the texts providing guidance for cancer therapy is *Cancer, Principles and Practice of Oncology*, 4th Edition, DeVita et al, Eds. J. B. Lippincott Co., Philadelphia, Pa. (1993). An appropriate therapeutic approach is chosen according to the particular type of cancer, and other factors such as the general condition of the patient, as is recognized in the pertinent field. A Bi-Fc can be added to a therapy regimen using other anti-neoplastic agents in treating a cancer patient.

In some embodiments, a Bi-Fc can be administered concurrently with, before, or after a variety of drugs and treatments widely employed in cancer treatment such as, for example, chemotherapeutic agents, non-chemotherapeutic, anti-neoplastic agents, and/or radiation. For example, chemotherapy and/or radiation can occur before, during, and/or after any of the treatments described herein. Examples of chemotherapeutic agents are discussed above and include, but are not limited to, cisplatin, taxol, etoposide, mitoxantrone (Novantrone®), actinomycin D, cycloheximide, camptothecin (or water soluble derivatives thereof), methotrexate, mitomycin (e.g., mitomycin C), dacarbazine (DTIC), anti-neoplastic antibiotics such as adriamycin (doxorubicin) and daunomycin, and all the chemotherapeutic agents mentioned above.

A Bi-Fc can also be used to treat infectious disease, for example a chronic hepatis B virus (HBV) infection, a hepatis C virus (HCV) infection, a human immunodeficiency virus (HIV) infection, an Epstein-Barr virus (EBV) infection, or a cytomegalovirus (CMV) infection, among many others.

A Bi-Fc can find further use in other kinds of conditions where it is beneficial to deplete certain cell types. For example, depletion of human eosinophils in asthma, excess human B cells in systemic lupus erythematosus, excess human Th2 T cells in autoimmune conditions, or pathogen-infected cells in infectious diseases can be beneficial. In a fibrotic condition, it can be useful to deplete cells forming fibrotic tissue.

Therapeutically effective doses of a Bi-Fc can be administered. The amount of Bi-Fc that constitutes a therapeutically dose may vary with the indication treated, the weight of the patient, the calculated skin surface area of the patient. Dosing of a Bi-Fc can be adjusted to achieve the desired effects. In many cases, repeated dosing may be required. For example, a Bi-Fc can be dosed twice per week, once per week, once every two, three, four, five, six, seven, eight, nine, or ten weeks, or once every two, three, four, five, or six months. The amount of a Bi-Fc administered on each day can be from about 0.0036 mg to about 450 mg. Alternatively, the dose can calibrated according to the estimated skin surface of a patient, and each dose can be from about 0.002 mg/m$^2$ to about 250 mg/m$^2$. In another alternative, the dose can be calibrated according to a patient's weight, and each dose can be from about 0.000051 mg/kg to about 6.4 mg/kg.

A Bi-Fc, or a pharmaceutical composition containing such a molecule, can be administered by any feasible method. Protein therapeutics will ordinarily be administered by a parenteral route, for example by injection, since oral administration, in the absence of some special formulation or circumstance, would lead to hydrolysis of the protein in the acid environment of the stomach. Subcutaneous, intramuscular, intravenous, intraarterial, intralesional, or peritoneal bolus injection are possible routes of administration. A Bi-Fc can also be administered via infusion, for example intravenous or subcutaneous infusion. Topical administration is also possible, especially for diseases involving the skin. Alternatively, a Bi-Fc can be administered through contact with a mucus membrane, for example by intra-nasal, sub-lingual, vaginal, or rectal administration or administration as an inhalant. Alternatively, certain appropriate pharmaceutical compositions comprising a Bi-Fc can be administered orally.

Having described the invention in general terms above, the following examples are offered by way of illustration and not limitation.

EXAMPLES

Example 1: Construction of Anti-CD3ε/HER2 and Anti-CD3ε/FOLR1 Bi-Fc Molecules and Single Chain Bispecific Molecules Bi-Fc molecules were generated using methods essentially described previously. Löffler et al. (2000), *Blood* 95(6): 2098-2103. In more detail, a construct encoding an anti-HER2/CD3 Bi-Fc was made as follows. DNA fragments encoding the VH region (SEQ ID NO:5) and the VL region (SEQ ID NO:6) of an anti-HER2 IgG antibody and the VH region (SEQ ID NO:7) and VL region (SEQ ID NO:8) of anti-human CD3 IgG antibody were amplified by PCR using forward and reverse primers and spliced together with flexible linkers. The resulting DNA fragment, which encodes a linear fusion DNA encoding two scFv's joined by a linker is referred to herein as the single chain anti-HER2/CD3 (SEQ ID NO:9). This construct was subcloned into a mammalian expression vector for antibody production.

An anti-HER2/CD3 Bi-Fc (SEQ ID NO:10) was constructed by fusing DNA encoding the single chain anti-HER2/CD3 to DNA encoding one of the two chains of an engineered human IgG1 Fc region. Specifically, DNA encoding an Fc polypeptide chain containing two positively charged mutations (D356K/D399K, EU numbering) plus alterations that inhibit FcγR binding (L234A and L235A) was fused to the DNA encoding the single chain anti-HER2/CD3 at the 3' end. The amino acid sequence of this anti-HER/CD3 Bi-Fc and the nucleic acid sequence encoding it are shown in SEQ ID NO:10 and 11, respectively. The second polypeptide chain that was part of the anti-HER2/CD3 Bi-Fc was a human IgG1 Fc polypeptide chain containing two negatively charged mutations (K392D/K409D, EU numbering) plus L234A and L235A, as shown in SEQ ID NO:12. DNA encoding this polypeptide (SEQ ID NO:13) was amplified and inserted into an appropriate vector for expression. Using similar methods, a single chain anti-FOLR1/CD3 (SEQ ID NO: 14) and an anti-FOLR1/CD3 Bi-Fc (SEQ ID NO:15) were constructed by replacing DNA encoding the anti-HER2 scFv fragment with DNA encoding an scFv fragment derived from an anti-human FOLR1 IgG antibody.

All single chain and Bi-Fc molecules described above were produced by transient transfection in human HEK 293-6E cells. The culture media was harvested after 6 days. The single chain anti-HER2/CD3 and anti-FOLR1/CD3 molecules were purified by nickel HISTRAP® (GE Healthcare Bio-Sciences, L.L.C., Uppsala, Sweden) column chromatography and eluted with a 25 to 300 mM imidizole gradient. The elution pools were further purified by size exchange chromatography (SEC) using a preparative SUPERDEX® 200 (GE Healthcare Bio-Sciences, L.L.C., Uppsala, Sweden) column, concentrated to >1 mg/mL, and stored at −70° C. Anti-HER2/CD3 Bi-Fc and anti-FOLR1/CD3 Bi-Fc molecules were purified using MABSELECT SURE™ (GE Healthcare Bio-Sciences, L.L.C., Uppsala, Sweden) affinity chromatography, eluting with 50 mM citrate, 1M L-Arginine, pH 3.5. The eluate was buffer-exchanged into formulation buffer by a preparative SEC with 10 mM potassium phosphate, 161 mM L-Arginine, pH 7.6 or with a solution containing acetate and sucrose with 150 mM NaCl, 161 mM L-Arginine, pH 5.2

Example 2: Testing BiTE:Fc Molecules for Binding to Target Cells and Immune Effector Cells Binding of the anti-HER2/CD3 Bi-Fc and single chain anti-HER2/CD3 to T cells expressing CD3 and JIMT-1 cells expressing HER2 was assessed as follows. Human pan-T cells (purified using Pan T Cell Isolation Kit II, human, Miltenyi Biotec, Auburn, Calif.) or purified JIMT-1 cells were incubated for 16 hrs at 4° C. in the absence or presence of 10 µg/mL of the anti-HER2/CD3 Bi-Fc or the single chain anti-HER2/CD3. Cell binding of the anti-HER2/CD3 Bi-Fc was detected using an allophycocyanin (APC)-labeled anti-human Fc secondary antibody. The single chain anti-HER2/CD3, which includes a FLAG® tag, was detected using a mouse anti-FLAG® antibody followed by an APC-labeled mouse Ig-specific antibody.

Figure 2:
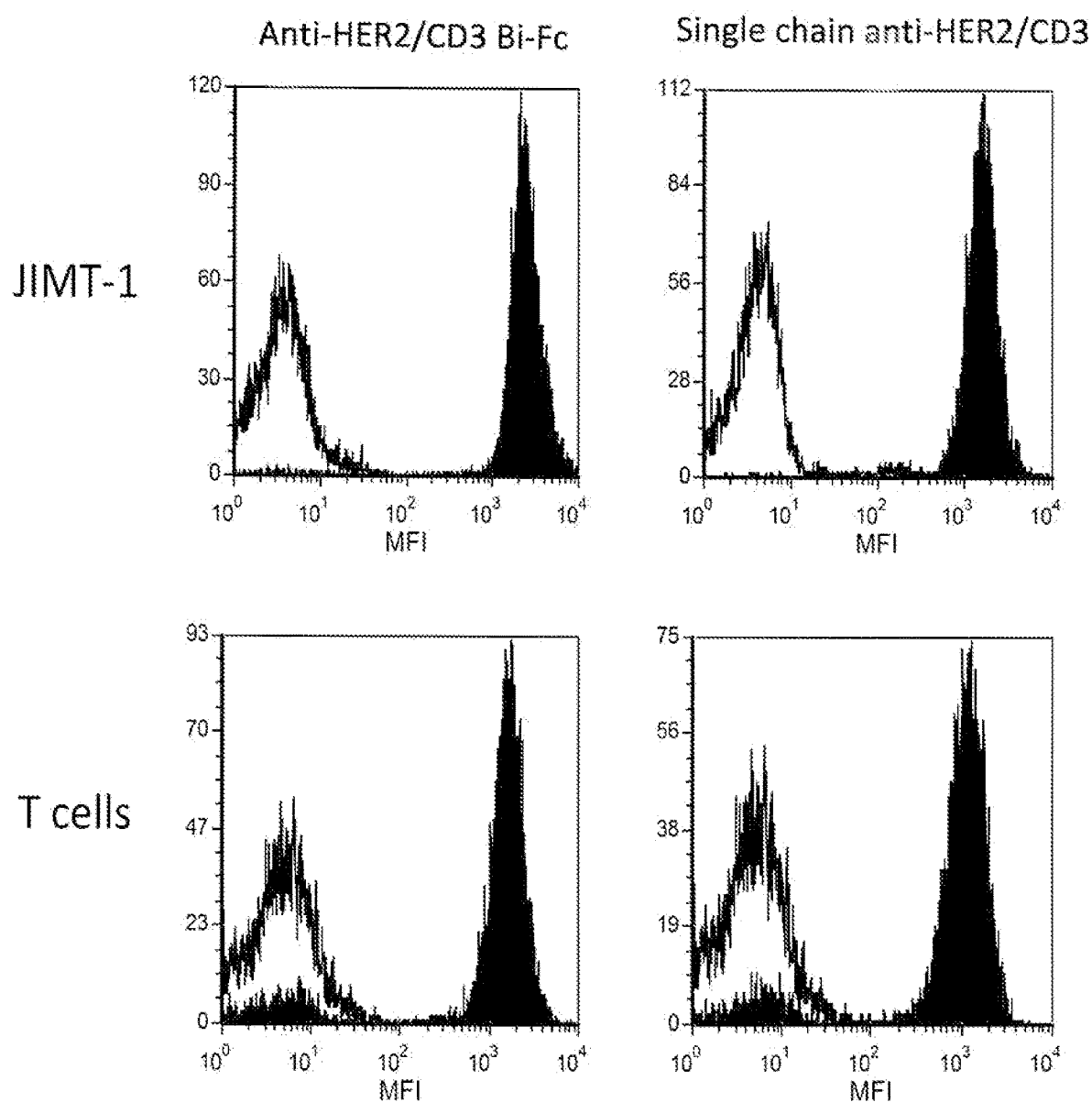
FIG. 2: Binding of a Bi-Fc to target cell and immune effector cells. Methods are described in Example 2. Mean fluorescence intensity (MFI) is indicated on the x axis, and the number of cells is indicated on the y axis. The unfilled profiles represent data from cells in the absence of one of the bispecific molecules, and the solidly filled profiles represent data from cells in the presence of one of the bispecific molecules. As indicated in the figure, panels at left represent data from samples containing the anti-HER2/CD3 Bi-Fc, and panels at right represent data from samples containing the single chain anti-HER2/CD3. Top two panels represent data from samples containing JIMT-1 cells (which express the target cell protein HER2), and bottom two panels represent data from samples containing T cells (which express the effector cell protein CD3ε).

In the fluorescence-activated cell sorting (FACS) histograms shown in FIG. 2, the unfilled profiles represent data from cells in the absence of one of the bispecific molecules, and the solidly filled profiles represent data from cells in the presence of one of the bispecific molecules, as indicated in the description of FIG. 2. These results indicate that the anti-HER2/CD3 Bi-Fc, as well as the single chain anti-HER2/CD3, binds to both T cells (expressing CD3) and to JIMT-1 cells expressing HER2.

Example 3: Lysis of Tumor Cell Lines in the Presence of Bi-Fc's and T Cells

Figure 3:
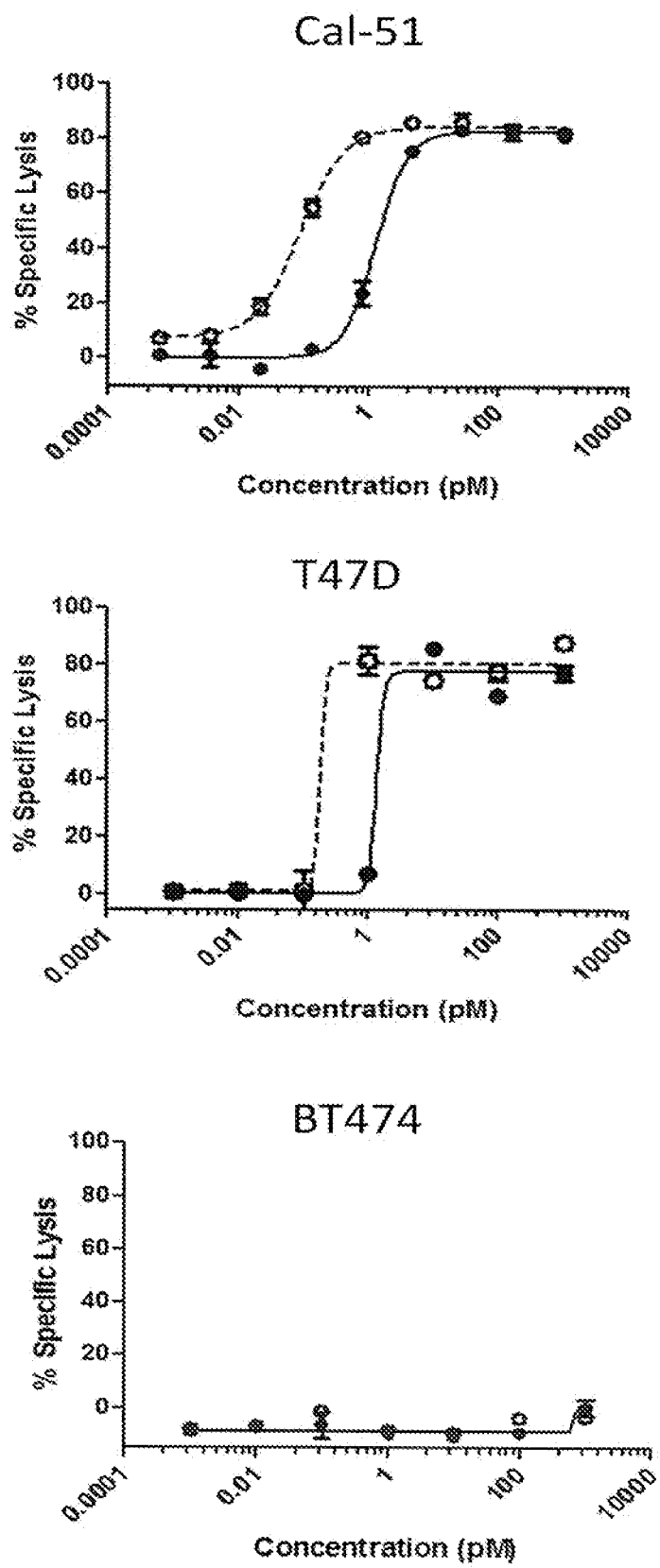
FIG. 3: Cytolytic activity of an anti-FOLR1/CD3 Bi-Fc and a single chain anti-FOLR1/CD3 molecule. Methods are described in Example 3. The x axis in each panel indicates the concentration of the Bi-Fc or single chain molecule (pM) in each sample. The y axis in each panel indicates the percent specific lysis calculated as described in Example 3. Open circles connected by a dashed line indicate data from samples containing the single chain molecule, and filled circles connected by a solid line indicate data from the Bi-Fc molecule. The top, middle, and bottom panels, as indicated, show data from Cal-51 cells (which express FOLR1), T47D cells (which express FOLR1), and BT474 cells (which do not express FOLR1), respectively.

The anti-HER2/CD3ε and anti-FOLR1/CD3ε Bi-Fc's and single chain anti-HER2/CD3ε and anti-FOLR1/CD3ε molecules described above were assayed to determine their activity in a T cell-dependent cell cytolysis (TDCC) assay using tumor cells expressing HER2 or FOLR1 as target cells. Briefly, pan T cells were isolated from healthy human donors using the Pan T Cell Isolation Kit II, human (Miltenyi Biotec, Auburn, Calif.). The T cells were incubated with CFSE-labeled tumor target cells at a ratio of 10:1 in the presence or absence of the anti-HER2/CD3ε or anti-FOLR1/CD3ε Bi-Fc's or the single chain anti-HER2/CD3ε or anti-FOR1/CD3 described in Example 1 at the varying concentrations as indicated in FIGS. 2 and 3. As a control, some samples contained T cells and tumor target cells, but no Bi-Fc or single chain molecule.

The target cells for the anti-HER2/CD3ε Bi-Fc and single chain molecule were either Cal-51 cells (expressing about 148,000 molecules of FOLR1 per cell), T47D cells (expressing about 101,000 molecules of FOLR1 per cell), or the control cell line BT474 (which did not express detectable levels of FOLR1).

The target cells for the anti-CD3ε/HER2 Bi-Fc and single chain molecules were JIMT-1 cells (expressing about 181,000 molecules of HER2 per cell), T47D cells (expressing about 61,000 molecules of HER2 per cell), or the control cell line SHP77 (which did not express detectable amounts of HER2).

After 39 to 48 hours of incubation, cells were harvested, and the percent of tumor cell lysis was monitored by uptake of 7-amino-actinomycin D (7-AAD), which stains double-stranded nucleic acids. Intact cells exclude 7-AAD, whereas 7-AAD can penetrate the membranes of dead and dying cells and stain the double-stranded nucleic acids inside these cells. Percent specific lysis was calculated according to the following formula:

% specific lysis=[% tumor lysis with Bi-Fc−% tumor cell lysis without bispecific/% of total cell lysis−% tumor cells lysis without bispeficic]× 100.

To determine percent total cell lysis, samples containing immune effector and labeled target cells without a Bi-Fc or single chain molecule were lysed with cold 80% methanol.

Results for the anti-FOLR1/CD3ε Bi-Fc and single chain molecule are shown in FIG. 3. Both the anti-FOLR1/CD3ε Bi-Fc and single chain molecule exhibited dose dependent lysis of both the Cal-51 and the T47D target cells. The $EC_{50}$ for each of these molecules in each of these cell lines is shown in Table 3 below.

TABLE 3

$EC_{50}$ of Bi-Fc and single chain anti-FOLR1/CD3 molecules

| Molecule | $EC_{50}$ (pM) Cell Line | | |
|---|---|---|---|
|  | Cal-51 | T47D | B7474 |
| Anti-FOLR1/CD3ε Bi-Fc | 1.27 | 1.35 | NA* |
| Anti-FOLR1/CD3ε single chain | 0.087 | 0.19 | NA* |

*NA means that there was little or no cell lysis detected.

These data indicate that both the anti-FOLR1/CD3ε Bi-Fc and single chain molecule can mediate lysis of cells expressing FOLR1 in the presence of T cells, but do not mediate lysis of cells not expressing FOLR1. The $EC_{50}$'s of the s Bi-Fc are about 10 fold higher than those of the single chain molecule, but they are still in the pM range. Thus, both the Bi-Fc and the single chain molecule are highly potent in this assay.

Figure 4:
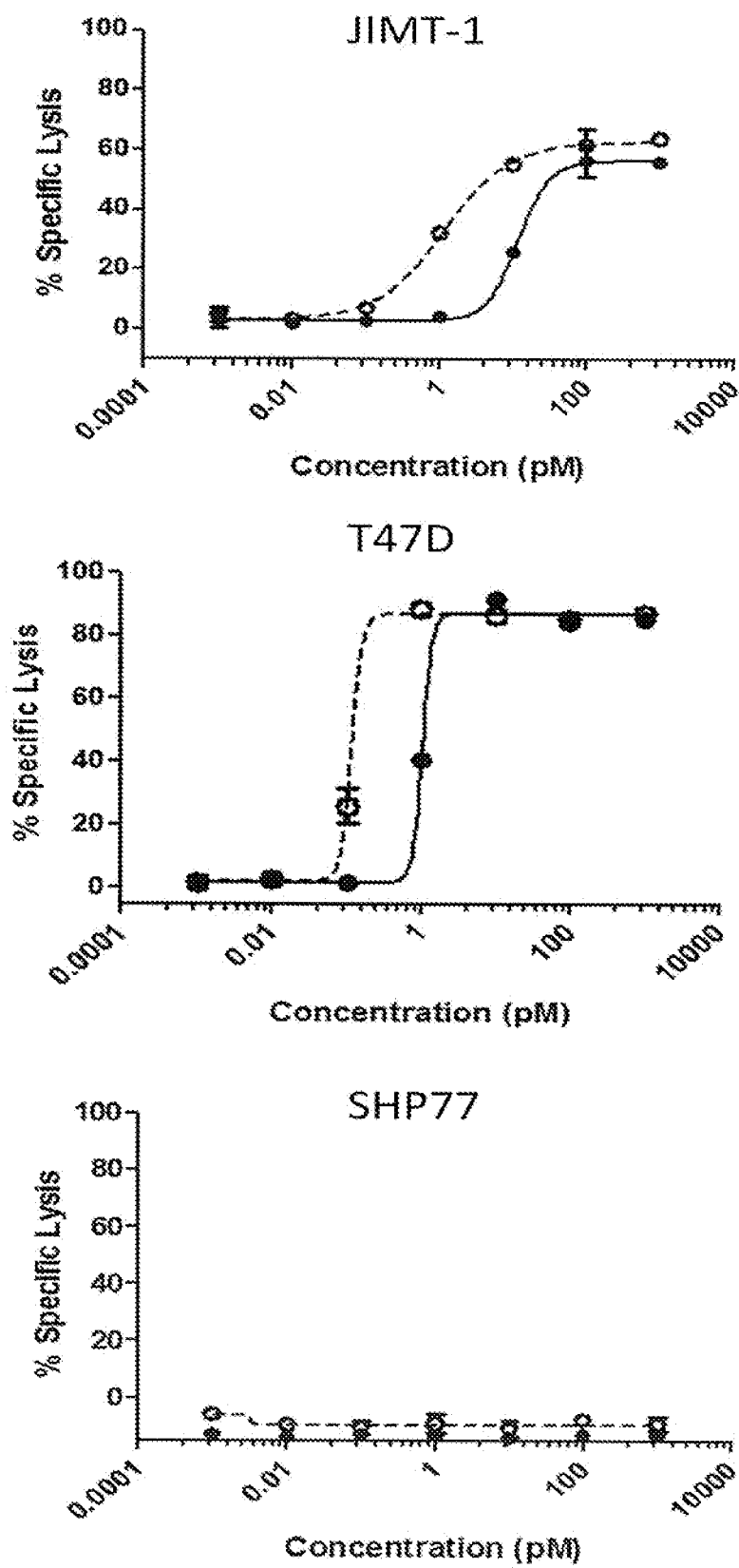
FIG. 4: Cytolytic activity of an anti-HER2/CD3 Bi-Fc and a single chain anti-HER2/CD3 molecule. Methods are described in Example 3. The x axis in each panel indicates the concentration of the Bi-Fc or single chain molecule (pM) in each sample. The y axis in each panel indicates the percent specific lysis calculated as described in Example 3. Open circles connected by a dashed line indicate data from samples containing the single chain molecule, and filled circles connected by a solid line indicate data from the Bi-Fc molecule. The top, middle, and bottom panels, as indicated, show data from JIMT-1 cells (which express HER2), T47D cells (which express HER2), and SHP77 cells (which do not express HER2), respectively.

Results for the anti-HER2/CD3ε Bi-Fc and single chain molecule are shown in FIG. 4. Both the anti-HER2/CD3ε Bi-Fc and single chain molecule exhibited dose dependent lysis of both the JIMT-1 and the T47D target cells, but no lysis of the control SHP77 cell line (which does not express HER2). The $EC_{50}$ for each of these molecules in each of these cell lines is shown in Table 4 below.

TABLE 4

$EC_{50}$ of Bi-Fc and single chain anti-FOLR1/CD3 molecules

| Molecule | $EC_{50}$ (pM) Cell Line | | |
|---|---|---|---|
|  | JIMT-1 | T47D | SHP77 |
| Anti-HER2/CD3ε BiFc | 11.52 | 1.03 | NA* |
| Anti-HER2/CD3ε single chain | 1.12 | 0.12 | NA* |

*NA means that there was little or no cell lysis detected.

These data indicate that both the anti-HER2/CD3ε Bi-Fc and single chain molecule can mediate lysis of cells expressing HER2 in the presence of T cells, but do not mediate lysis of cells not expressing HER2. The $EC_{50}$'s of the BiFc's are about 10 fold higher than those of the single chain molecule.

Example 4: Release of Cytokines by T Cells in the Presence of Bi-Fc and Target Cells The anti-HER2/CD3ε single chain and Bi-Fc and the anti-FOLR1/CD3ε single chain and Bi-Fc described above were assayed to determine whether they could stimulate the production of inflammatory cytokines by T cells. Briefly, twenty four hour cell culture supernatants from the TDCC assays like those described in Example 3 were assessed for cytokine concentrations using the Human TH1/TH2 7-Plex and Human Proinflammatory 14-Plex ultra Sensitive Kits from Meso Scale Diagnostics, L.L.C. Assays were performed according to the manufacturer's directions.

Figure 5A:
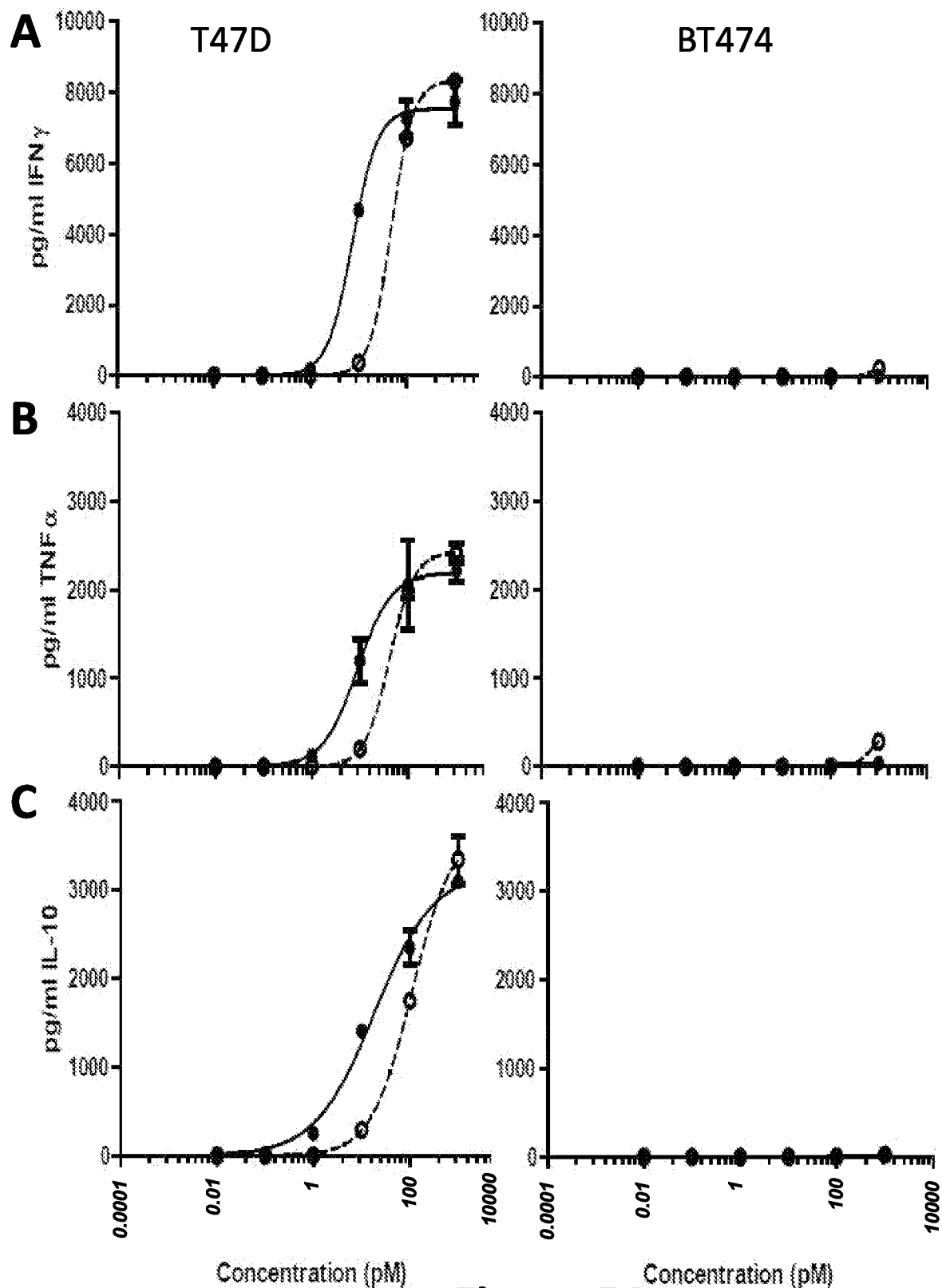
FIGS. 5A and 5B: Cytokine production by T cells in the presence of an anti-FOLR1/CD3 Bi-Fc or single chain molecule. Methods are described in Example 4. Open circles connected by dashed lines indicate data from assays containing the anti-FOLR1/CD3 Bi-Fc, and solidly filled circles connected by solid lines indicate data from the single chain anti-FOLR1/CD3 molecule. The x axis in each panel indicates the concentration of the Bi-Fc or single chain molecule (pM) in each assay. The y axis indicates the concentration and identity of the cytokine detected (pg/mL).
Figure 5B:
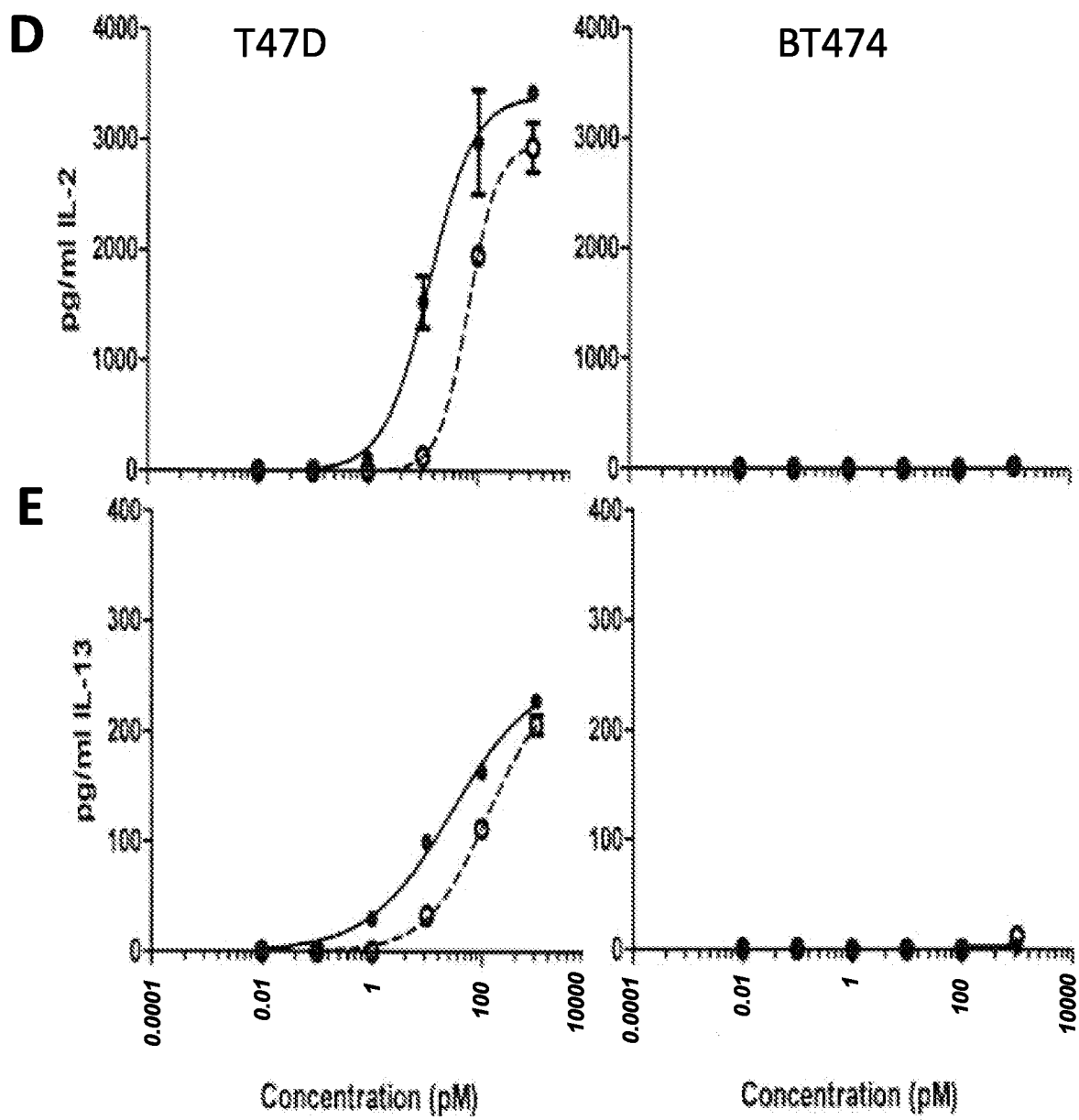
Figure 6A:
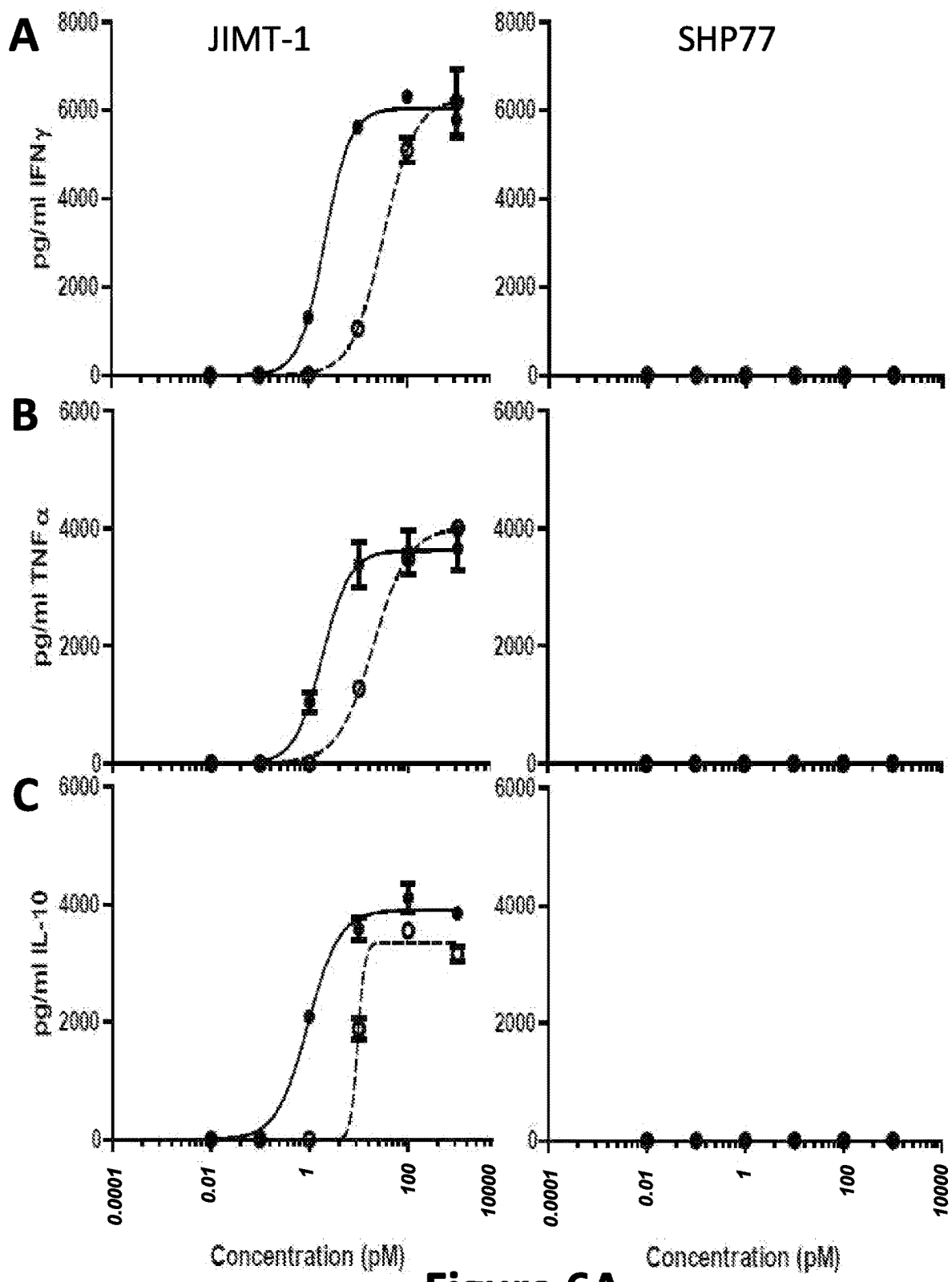
FIGS. 6A and 6B: Cytokine production by T cells in the presence of an anti-HER2/CD3 Bi-Fc or single chain molecule. Methods are described in Example 4. Open circles connected by dashed lines indicate data from assays containing the anti-HER2/CD3 Bi-Fc, and solidly filled circles connected by solid lines indicate data from the single chain anti-HER2/CD3 molecule. The x axis in each panel indicates the concentration of the Bi-Fc or single chain molecule (pM) in each assay. The y axis indicates the concentration and identity of the cytokine detected (pg/mL).
Figure 6B:
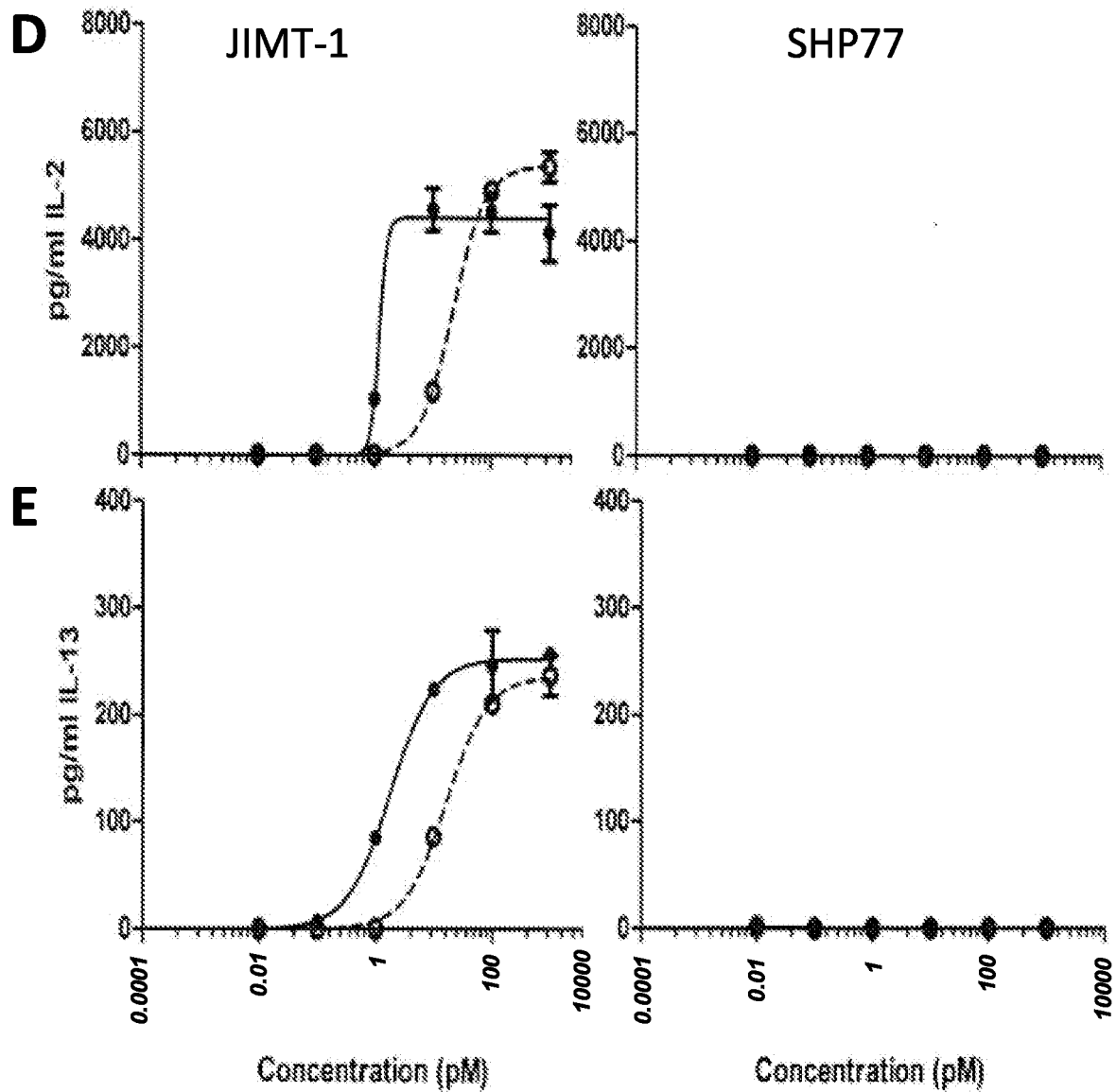

These results are shown in FIGS. 5A, 5B, 6A, and 6B. As shown in FIGS. 5A and 5B, the T cells secreted cytokines in the presence of the anti-FOLR1/CD3ε Bi-Fc or single chain in the presence of cells expressing FOLR1 (T47D, left panels), but not in the presence of cells that did not express FOLR1 (BT474, right panels). Similarly, as shown in FIGS. 6A and 6B, T cells secreted cytokines in the presence of the anti-HER2/CD3ε Bi-Fc or single chain in the presence of cells expressing HER2 (JIMT-1, left panels), but not in the presence of cells that did not express HER2 (SHP77). Thus, the secretion of interferon gamma (IFN-γ), tumor necrosis factor alpha (TNF-α), interleukin-10 (IL-10), interleukin-2 (IL-2), and interleukin-13 (IL-13) by T cells in the presence of a Bi-Fc or single chain molecule was dependent on the presence of cells expressing a target cell protein. Hence, activation of the T cells by the Bi-Fc's and single chain molecules was specific in the sense that it occurred only in the presence of target cells expressing a target cell protein.

In addition, the Bi-Fc's had very potent activity in the assay, exhibiting $EC_{50}$'s in the pM range as shown in the table below.

TABLE 5

$EC_{50}$'s for eliciting cytokine secretion

| | $EC_{50}$ (pM) | | | |
|---|---|---|---|---|
| | JIMT-1 cells | | T47D cells | |
| Cytokine | anti-HER2/ CD3ε Bi-Fc | anti-HER2/ CD3ε single chain | anti-FOLR1/ CD3ε Bi-Fc | anti-FOLR1/ CD3ε single chain |
| IFN-γ | 32.9 | 2.1 | 48.6 | 7.5 |
| TNF-α | 19.5 | 1.8 | 41.2 | 8.8 |
| IL-10 | 9.6 | 0.9 | 110.1 | 18.4 |
| IL-2 | 22.3 | 1.2 | 67.3 | 12.9 |
| IL-13 | 16.4 | 1.8 | 126.9 | 28.1 |

Thus, even though the Bi-Fc is almost twice the size of the single chain molecule, it remains a very potent activator of cytokine secretion by T cells in the presence, but not in the absence of, target cells. In addition, the Bi-Fc and the single chain molecule show a very similar cytokine profile.

Example 5: Upregulation of T Cell Activation Markers in the Presence of Bi-Fc and Target Cells The following experiment was done to determine whether a Bi-Fc could activate T cells in the presence of peripheral blood mononuclear cells (PBMC) and in the presence or absence of target cells. PBMC from healthy donors were purified on a FICOLL™ gradient from human leukocytes purchased from Biological Specialty Corporation of Colmar, Pa. These PBMC were incubated with the anti-HER2/CD3ε Bi-Fc or the single chain anti-HER2/CD3 bispecific molecule described above in the presence or absence of JIMT-1 cells at a 10:1 ratio. After 48 hours of incubation, non-adherent cells were removed from the wells and divided into two equal samples. All samples were stained with fluorescein isothiocynate (FITC)-conjugated anti-human CD3 antibody plus an allophycocyanin (APC)-conjugated anti-CD25 or anti-CD69 antibody. CD25 and CD69 are markers of activation of T cells.

Figure 7:
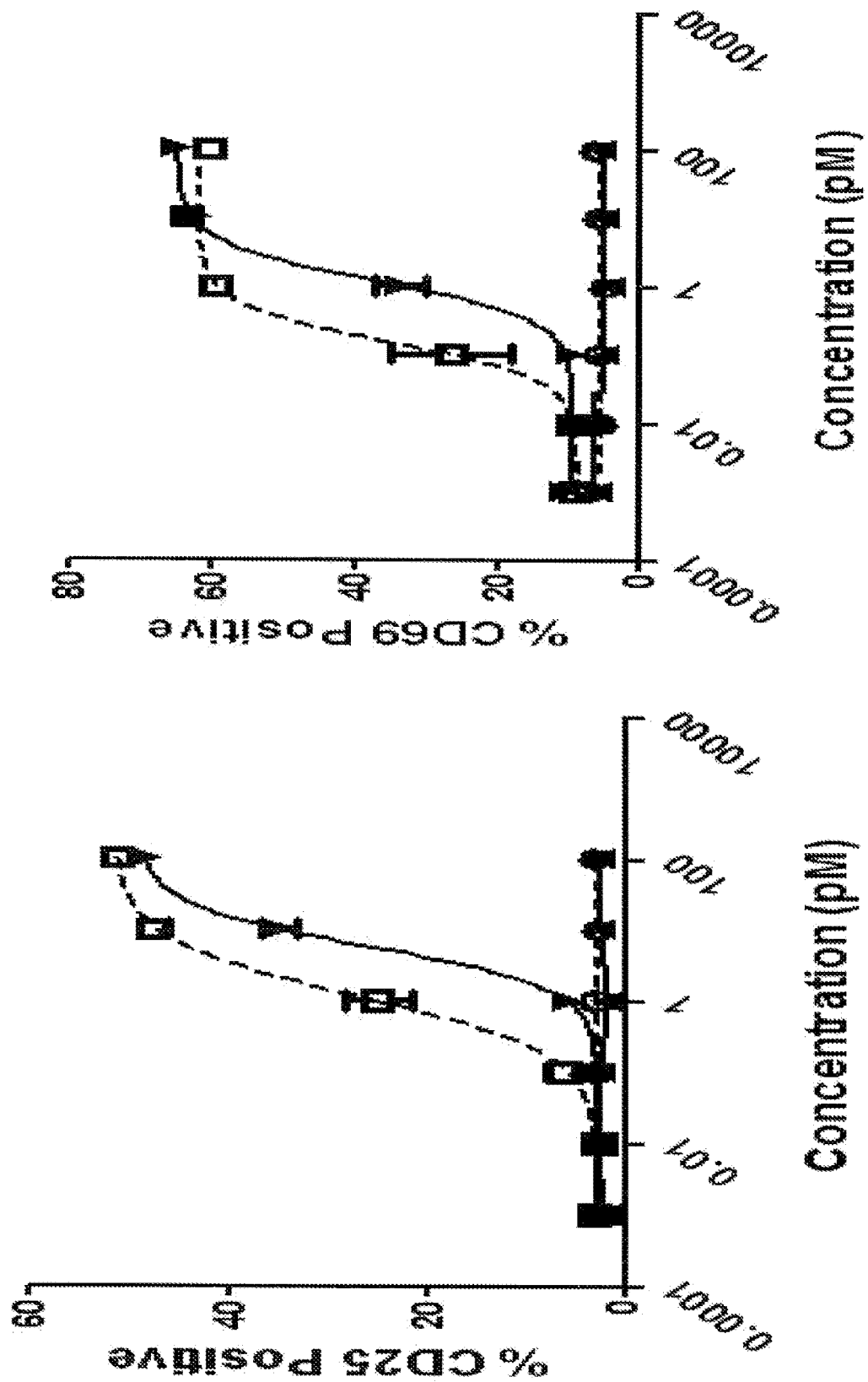
FIG. 7: Percentage of CD25+ and CD69+ cells in the presence of an anti-HER2/CD3 Bi-Fc or single chain molecule. Methods are described in Example 5. The x axis indicates the concentration (pM) of the anti-HER2/CD3 Bi-Fc or single chain molecule. The y axis indicates the percent of CD3+ T cells that are also CD25+ (left panel) or CD69+ (right panel) cells. Symbols indicate as follows: open squares connected by dashed line, the single chain molecule plus JIMT-1 target cells; solidly filled, downward pointing triangles connected by a solid line, the Bi-Fc molecule plus JIMT-1 target cells; open circles connected by a dashed line, the single chain molecule without JIMT-1 target cells; and solidly filled, upward pointing triangles connected by a solid line, the Bi-Fc without JIMT-1 target cells.

Up-regulation of CD25 and CD69 (FIG. 7) activation markers by $CD3^+$ peripheral T cells was observed with the anti-HER2/CD3ε Bi-Fc and the anti-HER2/CD3 single chain in the presence, but not in the absence, of HER2-expressing JIMT-1 tumor target cells. These observations suggest that T cell activation by the Bi-Fc is dependent on the presence of tumor target cells expressing the target cell protein and that activation of T cells in the peripheral blood through cross-linking by FcγR's in the presence of a Bi-Fc, similar to the anti-HER2/CD3ε Bi-Fc, likely not occur. The Fc region of the anti-HER2/CD3ε Bi-Fc contains alterations that inhibit binding to FcgRs.

Example 6: Pharmacokinetic Properties of Bi-Fc's

In the following experiment, the single dose pharmacokinetic profiles of an anti-HER2/CD3ε Bi-Fc (comprising the amino acid sequences of SEQ ID NOs:10 and 12) and an anti-HER2/CD3ε single chain (comprising the amino acid sequence of SEQ ID NO:9) was assessed by intravenous and subcutaneous bolus administration in male NOD.SCID mice (Harlan, Livermore, Calif.). These test molecules were injected as a bolus at 1 mg/kg intravenously via the lateral tail vein in some mice or subcutaneously under the skin over the shoulders in others. Serial bleeds of approximately 0.1 mL of whole blood were collected at each time point via retro-orbital sinus puncture. Upon clotting of whole blood the samples were processed to obtain serum (~0.040 mL per sample). Serum samples were analyzed by immunoassay using the technology Gyros AB (Warren, N.J.) to determine the serum concentrations of the anti-HER2/CD3ε single chain and Bi-Fc. Serum samples were collected at 0, 0.5, 2, 8, 24, 72, 120, 168, 240, 312, 384, and 480 hours. Serum samples were maintained at −70° C. (±10° C.) prior to analysis. Pharmacokinetic parameters were estimated from serum concentrations using non-compartmental analysis using Phoenix® 6.3 software (Pharsight, Sunnyvale, Calif.).

Figure 8:
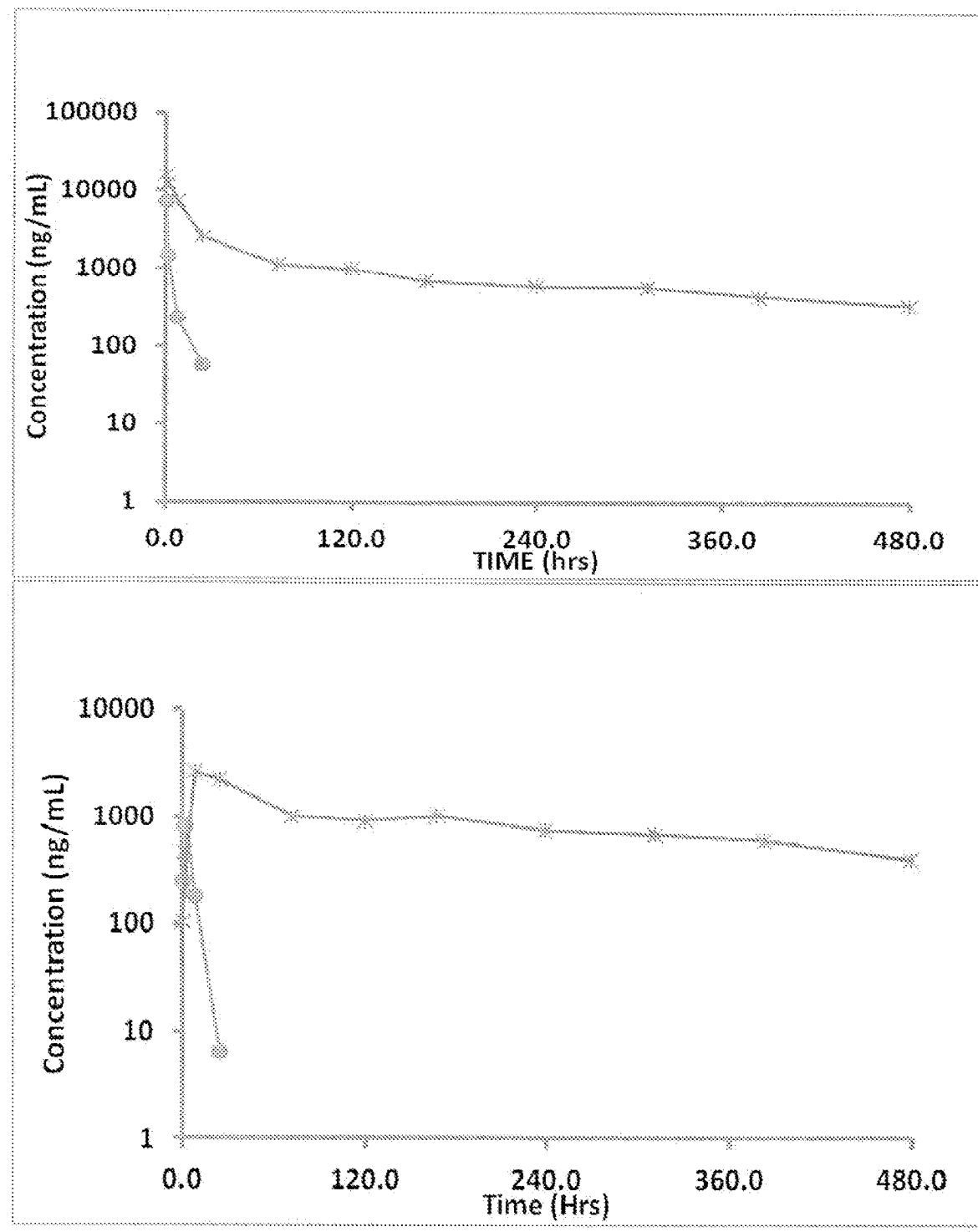
FIG. 8: Pharmacokinetic properties of a Bi-Fc and a single chain bispecific molecule in mice. Methods are described in Example 6. In the top panel, a pharmacokinetic profile following an intravenous injection is shown, and below is shown the profile following a subcutaneous injection. Solidly filled circles connected by a solid line indicate data from the anti-HER2/CD3 single chain molecule, and asterisks connected by a solid line indicate data from the anti-HER2/CD3 Bi-Fc molecule.

The single dose pharmacokinetic profiles of the Bi-Fc and the single chain molecule are shown in FIG. 8. The Bi-Fc showed an extended serum half life (219 hours) compared to the single chain molecule, which was rapidly eliminated and had a half life of only 5 hours. Exposure of the Bi-Fc was characterized by an area under the curve (AUC) of 524 hr*μg/mL, as compared to 19 hr*μg/mL for the single chain molecule. The subcutaneous bioavailability of the Bi-Fc was 83%, while that of the single chain molecule was 29%. Thus, the Bi-Fc showed favorable single dose pharmacokinetic properties as compared to the single chain molecule.

What is claimed is:

1. A bispecific-Fc molecule (Bi-Fc) monomer which mediates cytolysis of a cancer cell by a T cell, wherein the Bi-Fc comprises a polypeptide chain comprising an amino acid sequence having the following formula: V1-L1-V2-L2-V3-L3-V4-L4-Fc or Fc-L4-V1-L1-V2-L2-V3-L3-V4; wherein two of V1, V2, V3, and V4 are heavy chain variable (VH) regions and the other two are light chain variable (VL) regions; wherein one VH region and one VL region binds CD3 epsilon on a T cell and one VH region and one VL region binds HER2 on the cancer cell; wherein Fc is a human IgG Fc polypeptide chain; wherein L1, L2, L3, and L4 are linkers; wherein L4 can be present or absent; and wherein the Bi-Fc monomer comprises a single chain anti-HER2/CD3 epsilon antibody comprising the amino acid sequence of SEQ ID NO: 9.

2. A pharmaceutical composition comprising the Bi-Fc monomer of claim 1 and a physiologically acceptable carrier, excipient, and/or diluent.

3. The Bi-Fc monomer of claim 1 comprising the amino acid sequence of SEQ ID NO: 10.

4. A bispecific-Fc molecule (Bi-Fc) monomer which mediates cytolysis of a cancer cell by a T cell, wherein the Bi-Fc comprises a polypeptide chain comprising an amino acid sequence having the following formula: V1-L1-V2-L2-V3-L3-V4-L4-Fc or Fc-L4-V1-L1-V2-L2-V3-L3-V4; wherein two of V1, V2, V3, and V4 are heavy chain variable (VH) regions and the other two are light chain variable (VL) regions; wherein one VH region and one VL region binds CD3 epsilon on a T cell and one VH region and one VL region binds FOLR1 on the cancer cell; wherein Fc is a human IgG Fc polypeptide chain; wherein L1, L2, L3, and L4 are linkers; wherein L4 can be present or absent; and wherein the Bi-Fc monomer comprises a single chain anti-FOLR1/CD3 epsilon antibody comprising the amino acid sequence of SEQ ID NO: 14.

5. The Bi-Fc monomer of claim 4 comprising the amino acid sequence of SEQ ID NO: 15.

6. A pharmaceutical composition comprising the Bi-Fc monomer of claim 3 and a physiologically acceptable carrier, excipient, and/or diluent.

7. A pharmaceutical composition comprising the Bi-Fc monomer of claim 4 and a physiologically acceptable carrier, excipient, and/or diluent.

8. A pharmaceutical composition comprising the Bi-Fc monomer of claim 5 and a physiologically acceptable carrier, excipient, and/or diluent.

* * * * *